United States Patent [19]
Bradley et al.

[11] Patent Number: 6,004,779
[45] Date of Patent: Dec. 21, 1999

[54] REGULATED GENE EXPRESSION IN YEAST

[75] Inventors: John D. Bradley, Brookline; Craig M. Thompson, Arlington; Jeffrey B. Moore, Chestnut Hill; C. Richard Wobbe; Judith M. Healy, both of Lexington; Caroline E. Donnelly, Bedford, all of Mass.

[73] Assignee: Scriptgen Pharmaceuticals, Inc., Waltham, Mass.

[21] Appl. No.: 09/138,024

[22] Filed: Aug. 21, 1998

Related U.S. Application Data

[60] Provisional application No. 60/056,719, Aug. 22, 1997.
[51] Int. Cl.$^6$ .............................. C12N 1/19; C12N 15/31; C12N 15/81; C12P 21/00
[52] U.S. Cl. ..................... 435/69.1; 435/254.2; 435/483
[58] Field of Search ................................ 435/69.1, 254.2, 435/483

[56] References Cited

PUBLICATIONS

Zarmik Moqtaderi et al., TBP–Associated Factors Are Not Generally Required For Transcriptional Activation In Yeast, *Nature*, vol. 383, pp. 188–191, Sep. 12, 1996.

Yu, W. et al., Molecular and Cellular Biology, 16:2464–2472, 1996.

*Primary Examiner*—Johnny F. Railey, II
*Attorney, Agent, or Firm*—Darby & Darby

[57] ABSTRACT

The invention provides novel yeast cells comprising genes whose expression can be modulated by growth in the presence or absence of metal ions, methods for making such yeast cells, and methods of using such yeast cells for determining the requirement for expression of particular genes for the growth or viability of the yeast cells.

18 Claims, 18 Drawing Sheets

FIG. 2A
A. SINGLE ROUND PCR STRATEGY (OLIGOS SYNTHESIZED):
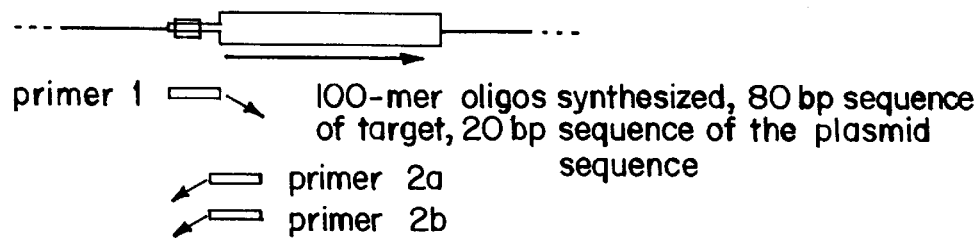
primer 1    100-mer oligos synthesized, 80 bp sequence of target, 20 bp sequence of the plasmid sequence
    primer 2a
    primer 2b
B. DOUBLE ROUND PCR STRATEGY (OLIGOS PRODUCED BY PCR)
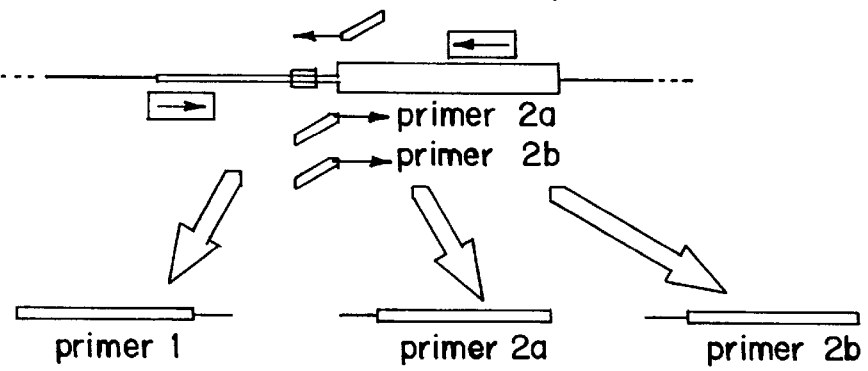
primer 2a
primer 2b
primer 1    primer 2a    primer 2b

II: TRANSFORMING DNA PRODUCED BY PCR WITH OLIGOS FROM STEP I:

III: TRANSFORMATION, RECOMBINATION

FIG. 4A

```
GAATTAATTCGAGCTCGGTACCCGGTGATCTTCGCTCGGCCACAAATCCCCTGGATATCATTGGCC
TGTCGAGGTATCGGCCGCGTGAACTACCGGAATTACTATGCAAAACAATTGGAAATCTGGTAG
GAAACCTTGTTCTAGAACTTGGCGATTGCTGACAAAGAAGAAAAGGCCTATTGTTGCTGCCTC
TTTGTTGTTCTTCCTCGTATTGTCTTGCCGGTGTTCTTTGTCTTTGTGTGTAGGTTCTTAC
TATTATAGTGCTCTTTGCTATTATATTTCTTCGTTTTCACTTTGCGTAATGTAACGGTCTTAAA
CAAAGTTTTTTTTTTTCGCTCTTGCATTTTCCATTTTCCTTTCTGCTCTATCTTATTTGCTAATGTAGT
TTCAGAAGTTTTACCTTAAATATAGCACTATTTTACGGTGTCTTAACTCTCCCCTCTTCACCCCCTCATTA
TTTATAATTTCGCATATAATTATACATTACGGTGTCTTAACTCTCCCCTCTTCACCCCCTCATTA
TTCCAGAAAATACTAATACTTCTTCACACAAAGAACGCAGTTAGACACAGTCTTCAATCAACAATGACTAGTA
GTTTTCTTGAACCAAAGAAAAGTCACCAGAGGCAATAGACTCTTCAATCTCATTGGTTGTTTT
TTGGCTTCTGCAGTGGACGAGAACTTGGCCTTTTGCCTAACTTCTCCTAACTTCCTCAATTGGTTTGTTTTT
TCTCTTGATTTGAGCATCCAATTGCTTAATAGAGTCGTGAATGTTGCTTCTACGTTCTTGTTGGTGGTA
CAGCTTGGATCTTGATGATCTCCTTGTTTCTCTAATTGCTGATTTCAGTTCAGTGTCGATTTTTTCAA
TCGTTGACCTGGTCTTGTCCAATTCCTTGTTCTCTAACGGAGACATCGGGCGCTTGAACTTGTGTT
TTGAACGTTAAGAGTGTCCAATTCTTCTGTCTCTAACGAAAATATGCTATTACGTTGATAAAGAGGAA
GTTGGGAGGACATGGCAATGGCTGTGTTGTTAGAACTGAATGACCAGAATGAGTGAAAAT
AGTGAAATCAGTTCAAAAATGCAAAATGAAAAAAAAAGATGAACCTAAAAACTCAATTGGCTTATAGACTCCGTC
GGAGATGGAGGGCAAAATGAAAAAAAAAGATGAACCTAAAAACTCAATTGGCTTATAAATGTT
GTACTTTAATGCTATGTATAACGCAACCAAGCAATTTCGAGATCAGTTATTTTTTTCACGCCACAGT
CGAGATAAAATGCGAATTACGTGTTCAACACCATTACAAGTTAGAATATTATCTATTAACATGCAGT
GCGGGTAAGCAATTTTCGCCTACGTTTAGTGAGTCAACAATGGTTCTGGGGCCCGATTCGTTCTCAATGCCAC
TATGTTTGTCACTTATATGACGTTATTTACAAGTTAGAATATTATCTATTAACATGCAGT
AGCCACGCTTACGTTTAGTGAGTCAACAATGGTTCTGGGGCCCGATTCGTTCTCAATGCCAC
CAAAGGGAATTTCGACGAAGAAGTCACTCCTCATCTTCAAATTCGTTCTTACGCCCCTTGGCTTTCG
TCCCCACCACTAGAACAACAACAGGCAGCTCGTTACATAATCGTTCAAATCGTGCATGCTAATAGT
TTTTCTTGTGATTTAGTAAAAACTCTAACGGTTATCAACGTAAAATATGGGCAGAAGTTCG
CCATTCTTGTGATTTAGTAAAAACTCTAACGGTTATCAACGTAAAATATGGGCAGAAGTTCG
AGGGCCCCACTGCTTGTCTTGGACACCAGGCGTCAAAGGAGAGCAGTTTCTTCTCGACATCAC
```

AATGAAGTCAACCCCCAGGAGAAGTAAGGCGCTTCTAATAATGGCACCGATATTGTGAGGGTCAGTTA
TTTCATCCAGATATAACCCGAGAGGAAACTTCTTAGCGTCTGTTTCGTACCATAAGGCAGTTCA
TGAGGTATATTTCGTTATTGAAGCCCAGCCTGTGAATGCTTAATGCTGTGAACTGGTGTCCAT
GTCGCCTAGTACGCAATCTCCACAGGCTGCAAAGGTTTGTCTCAAGAGCAATGTTATTGTGCA
CCCCGTAATTGGTCAACAAGTTAATCTGTGCTTGTCGTCGTAACCTTCAGTTCA
TCGACTATCTGAAGAAATTACTAGGAATAGTGCCATGGTACAGCAACCGAGAATGGCAATTTCT
ACTCGGGTTCAGCAACGCTGCATAAACGCTGTTGGTGCCGTAGACATATTCGAAGATAGGATTAT
CATTCATAAGTTCAGAGCAATGTCCTTATTCTGGAACTTGGATTTATGGCTCTTTTGGTTTAAT
TTCGCCTGATTCTTGATCTCTTTAGCTTCTCGACGTGGGCCTTTTCTTGCCATATGGATCTGA
ATTCTAGTCTTTTTGCTGGAACGGTTGAGCGGAAAAGACGCATCGAATTCGAATTCTTCGAGCTCGTTAGCGA
TTGGCATTATCACATAATGAATTATACATTATATAAAGTAATGTGATTTCTTCGAAGAATATACT
AAAAAATGAGCAGGCAAGATAAACGAAGGCAAAGCGCATTATTCTGTTCAGACAGCACTACCACAGGAT
TCTACACCTAAGATTCCAAGACCCAAGGTGTGGAAATACCCCATAATTCAAACATTTCTAAAATTA
CTTAATAGAGCGAATGACGCGCTCAAGGTGTTACAACCGGAATAAGGCACACTGGGAAATCTAGCGGAGAAG
TTGGTACGAAGTGGAAGGCTTACAACATGAAAGGAAGTATCCTGAATACAAATACAAGCCGGTAAGAAAGTCTAAGAA
GAGAAACTAGAACATGAAGGAAGTATCCTGAATACAAATACAAGCCGGTAAGAAAGTCTAAGAA
GAAGCAACTACTTTTGAAGGAAATCGAGCAACAGCCCTTAACAACAATATAGTTCTTATGAAAGAGCA
AGAAACAGTCACAACCGCAATTACAACAGCCCTTAACAACAGCAGCTATCAGTTCCAATGGAACAATGA
CATTCTCTTTCACCATTCCCTCGGTGTCAAGCTCGAACAGCTATCAGTATGGTCTCCAGATCCTCTAGAG
TCTTAAGAGGTTGCCTATTCCTTCTTTCTGTTAATACTTCTAACTATATGGTCTCCAGATCCTCTAGAG
TCGACCTGCAGGCATGCAAGCTTGGCGTAATCATGGTCATATAAGCTGTTTCCTGTGTGAAATTGTTA
TCCGCTCACAATTCCACACAACATACGAGCCGGAAGCATAAAGTGTAAAGCCTGGGGTGCCTAAT
GAGTGAGCTAACTCACATTAATTGCGTTGCGCTCACTGCCGCTTTCCAGTCGGGAAACCTGTCG
TGCCAGCGGGATCCACTAGTTCTAGAGTCGACCGGCATGCAAGCTTGGCGTAATCATGGTCATA
GCTGTTTCCTGTGTGAAATTGTTATCCGCTCACAATTCCACACAACATACGAGCCGGAAGCATAA
AGTGTAAAGCCTGGGGTGCCTAATGAGTGAGCTAACTCACATTAATTGCGTTGCGCTCACTGCCC

FIG. 4C

```
GCTTCCAGTCGGGAAACCTGTCGTGCCAGCTGCATTAATGAATCGGCCAACGCGCGGGGAGAGG
CGGTTGCGTATTGGGCGGTATCAGCTCACTCAAAGGCGGTAATACGGTTATCCACAGAATCAGGGATAAC
TGCGGCGAGCGGTATCAGTGTGAGCAAGAACATGTGAGCAAAAGGCCAGCAACGTAAAAAGGCCGCGTTGCT
GCAGGAAAGAACATGTGAGCAAAAGGCCAGCAACGGTAAAAAGGCCGCGTTGCT
GGCGTTTTCCATAGGCTCCGCCCCCCTGACGAGCATCACAAAAATCGACGCTCAAGTCAGAGGT
GGCGAAACCCGACAGGACTATAAAGATACCAGGCGTTTCCCCCTGGAAGCTCCCTCGTGCGCTCT
CCTGTTCCGACCCTGCCGCTTACCGGATACCTGTCCGCCTTTCTCCCTTCGCTCCAAGCTGGGCTGTG
TTCTCATAGCTCACGCTGTAGGTATCTCAGTTCGGTGTAGGTCGTTCGCTCCAAGCTGGGCTGTG
TGCACGAACCCCCCGTTCAGCCGACCGCTGCGCCTTATCCGGTAACTATCGTCTTGAGTCCAAC
CCGGTAAGACACGACTTATCGCCACTGGCAGCAGCCACTGGTAACAGGATTAGCAGAGCGAGGTA
TGTAGGCGGTGCTACAGAGTTCTTGAAGTGGTGGCCTAACTACGGCTACACTAGAAGGACAGTAT
TTGGTATCTGCGCTCTGCTGAAGCCAGTTACCTTCGGAAAAAGAGTTGGTAGCTCTTGATCCGGC
AAACAAACCACCGCTGGTAGCGGTGGTTTTTTTGTTTGCAAGCAGCAGATTACGCGCAGAAAAAA
AGGATCTCAAGAAGATCCTTTGATCTTTTCTACGGGGTCTGACGCTCAGTGGAACGAAAACTCAC
GTTAAGGGATTTTGGTCATGAGATTATCAAAAAGGATCTTCACCTAGATCCTTTTAAATTAAAA
TGAAGTTTTAAATCAATCTAAAGTATATATGAGTAAACTTGGTCTGACAGTTACCAATGCTTAAT
CAGTGAGGCACCTATCTCAGCGATCTGTCTATTTCGTTCATCCATAGTTGCCTGACTCCCCGTCG
TGTAGATAACTACGATACGGGAGGGCTTACCATCTGGCCCCAGTGCTGCAATGATACCGCGAGAC
CCACGCTCACCGGCTCCAGATTTATCAGCAATAAACCAGCCAGCCGGAAGGGCCGAGCGCAGAAG
TGGTCCTGCAACTTTATCCGCCTCCATCCAGTCTATTAATTGTTGCCGGGAAGCTAGAGTAAGTA
GTTCGCCAGTTAATAGTTTGCGCAACGTTGTTGCCATTGCTACAGGCATCGTGGTGTCACGCTCG
TCGTTTGGTATGGCTTCATTCAGCTCCGGTTCCCAACGATCAAGGCGAGTTACATGATCCCCCAT
GTTGTGCAAAAAAGCGGTTAGCTCCTTCGGTCCTCCGATCGTTGTCAGAAGTAAGTTGGCCGCAG
TGTTATCACTCATGGTTATGGCAGCACTGCATAATTCTCTTACTGTCATGCCATCCGTAAGATGC
TTTTCTGTGACTGGTGAGTACTCAACCAAGTCATTCTGAGAATAGTGTATGCGGCGACCGAGTTG
CTCTTGCCCGGCGTCAATACGGGATAATACCGCGCCACATAGCAGAACTTTAAAAGTGCTCATCA
TTGGAAAACGTTCTTCGGGGCGAAAACTCTCAAGGATCTTACCGCTGTTGAGATCCAGTTCGATG
TAACCCACTCGTGCACCCAACTGATCTTCAGCATCTTTTACTTTCACCAGCGTTTCTGGGTGAGC
```

FIG. 4D

```
AAAAACAGGAAGGCAAAATGCCGCAAAAAAGGGAATAAGGCCGACACGGAAATGTTGAATACTCA
TACTCTTCCTTTTCAATATTATTGAAGCATTTATCAGGGTTATTGTCTCATGAGCGGATACATA
TTTGAATGTATTTAGAAAAATAAACAAATAGGGGTTCCGCGCACATTTCCCGAAAGTGCCACC
TGACGTCTAAGAGAACCATTATTATCATGACATTAACCTATAAAATAGGCGTATCACGAGCCAG
CTTTCAATTCAATTCATCATTTTTTTTTATTCTTTTTTTGATTTCGGTTTCTTTGAAATTT
TTTGATTCGGTAATCTCCGAACAGAAGAAGAACATGAAAATGCCCAGTATTCTTAACCTGCACAGAA
TATACGCATATGTAGTGTTGAAGAACGAAGATAAATCATGTCGAAAGCTACATATAAGGAACGTGCTACT
CAAAAACATGCAGGAAACGAAGATAAATCATGTCGAAAGCTACATATAAGGAACGTGCTACT
CATCCTAGTCCTGTGCTGCTACCACCAGATGTTCGATCATTTAATATCACGAAAAGCAAACAAACTTGTGC
TTCATTGGATGTTCGTACCACCACATGTGGATATCTTGACTGATTTTCCATGGAGGCACAGTTAAGCCGCTA
GTTTACTAAAAACACATGTGGATACAATTTTTTACTCTTCGAAGACAGAAATTGCTGACATTGGTAA
AAGGCATTATCCGCCAAGTACTACTCTCGCGGTTATTGTTAGCGGGTTAGCGGTATTGTTAGCAGAAGAATG
TACAGTCAAATTGCAGTAGTCCTCTCGCGGGCCCAGTATTGTTAGCGGTGTTGAAGCAGGGCGCAGAAGAATG
CACACGGTGTGGTGGGCCCAGTATTGTTAGCAGAATGTCAAGGCGCTCCCTATCTACTGGAGAATA
GAACCTAGAGGCCTTTTGATGTTAGCAGAATGTCAAGGCGCTCCCTATCTACTGGAGAATA
TACTAAGGGTACTGTTGACATTGCGAAGAGCGACAAAGATTTTGTTATCGGCTTTATTGCTCAAA
GAGACATGGGTGGAAGAGAGATGAAGGTTACGATTGGTTGATTATGATGACACCCGGTGTGGGTTTAGAT
GACAAGGGAGACGCATTGGTGAAGAGACTATTTGCAAAGGGAAGGATGCTAAGGTAGAGGGTGAACGTT
CATTATTATTGTTGGAAGAGACTATTTGCAAAGGGAAGGATGCTAAGGTAGAGGGTGAACGTT
ACAGAAAAAGCAGGCTGGGAAGCTATACTAAACTCACAAATTGAGAAGAATGCGCCAGCAAAACTAAAAACTGTATTA
TAAGTAAATGCATGTATACTAAACTCACAAATTGAGACGTGAAAACCTCTGACACATGCAGCTCCCGAG
CGCCCTTTCGTCTCGCGCGTTTCGTGATGACGTGAAAACCTCTGACACATGCAGCTCCCGAG
ACGGTCACAGCTTGTCTGTAAGCGGATGCCGGGAGCAGACAAGCCCGTCAGGCGTCAGCGGG
TGTTGGCGGTGTCAGGGTCTGGCTTAACTATGCGCTTAACTACTGCGCATCGAGATTGTACTGAGAGTGCACC
ATATGCGGTGTGAAATACCGCACAGATGCGTAAGGAGAAAATACCGCATCAGGCGCCATTCGCCA
TTCAGGCTGCCAACTGTTGGGAAGGCGATCGGTGCGGGCCTCTTCGCTATTACGCCAGCTGGC
GAAAGGGGGATGTGCTGCAAGGCGATTAAGTTGGGTAACGCCAGGGTTTTCCCAGTCACGACGTT
GTAAAACGACGGCCAGT
```

FIG. 5A

```
GAATTAATTCGAGCTCGGTACCAGTTGCCACACCACAAAGTCGAAAAAGGCTAAGAAACCAAAGAATAA
GGTACTAAGTACCCAGGCGCTACTAAGACCAACGAGATTGCCACGAACTAGAGGAAACCAAATTGTAAG
CATAGCTTAATCCGTTTTCACGATTCATAATATAATAAGAAAAAGATATATCATATAAACGTTATAA
AATTAATAACCGGGTAAGTGTAGAAAAGTGATGCGACGGTTTATTTCTCCTCTGCGATTGAATTT
AACTTGCAGATAGTGACCATAAGGCAACTACCCAGTGCAAACAGTTTGATAACGCCCAGTACATCAAC
GAGCGAGTATAAAGACTTGGTACATTTAAAAGGAAACATATATGTTTCATTGCTAGACCCTTTTA
GTCTCACCTCAATAAACTGCTTTTATTCCTCATTGGCTTTCTTAATTTGCATACTTATAGCG
TGAAACTGGGCATTTAACAAAAGCAAACTATTTTAATAGTCCTCCTTTCTTCTTCGGACAAAGGCAGT
ATTGCGATACATTATTAAGTTTTTTTACCACCTTTCTTCTTCCTCACTGAAGTCCCTAATCTTACAGTCACACA
TGAAGTTTACTGTATCCTATTAGTGACTATTTTTCTTGAACCAAAGAAAAGGTCACCAGGCAATAGACTCT
AATTACATAGAACATTCCAACTAGTAGTTTTTTCTGGCTTCTGCAGTGACGAACTTGCCTTTTGCCTAACTTCTCCT
TCAATCTCATTGATTCTTTGCTCTCTTGATTGAGCATCTCCTTGCTTTCTATCCTGTGTTCTTACGATTTCAGTGTCGATTTCA
CAATTTGGTGTTTTCTCTCTGGATCTGATTGATCGATTTGCTTTAGAAATAAACCGATTCGGGCGCTTGAACTTGTCGTTCTACG
GTGGTATCGTTGACCTGGTGTGTTGCCAATTTCTTGTCTTTAGAAAATATGCTATTACGTTGATAAAGGAGGAAGGTGAAAT
ATTGAACGTTAAGAGTGTCAATGGCTGTGTGTTGTTAGAACGAAGAATGACTTGGGCGCTTGATAAAGGAGGAAAATGGAGGGCC
AAATGAAAAAAAAAAGATGAACTAAAATTTCGAAACTCAATTGTTTTTCACGCCACAGTGCGGGTAAGCAATTTTCGCTACCACCA
AACGCAACCAAGCAATTTCGAGATCAGTTATTTTTCACGCCACAGTGCGGGTAAGCAATTTTCGCTACCACCA
CCATTACACATGTATATATAATCAATGCCACCAAAGGAATTTCGACGAAGAAGTCACTCCTCATCTTCAAATTC
AGTTAGAGAATATTATCTATTAACAATGCCACCAAAGGAATTTCGACGAAGAAGTCACTCCTCATCTTCAAATTC
GGCCCGATTGCCTTTCTCAATGTAGTTTTTTCCAACAGTGTATTTTCGACGTTGACGTTGTAATAAA
GTTCTTACGCCCTGGCTTTCGTTGTGACCAGTGTATTTTCGACGTTGACGTTGTAATAAA
CGTGCATGCTAATAGTTTTTTCCAACAGTGTATTTAGTAAAAAACTTAAGGCGTTTATCAACGTAAATATGGCAGA
AGTTCGAGGGCCCACCATTCTTGTGATTTGGACACCAGGCGTCAAAGGAGAGCAGTTTCTTCTCGACATCA
```

FIG. 5B

```
CAATGAAGTCAACCCCCAGGAAGTAAGCGCTTCTAATAATGGCACCGATATTGTGAGGTCAGTTATTTC
ATCCAGATATAACCGAGAGAGAAACTTCTTAGCGTCTGTTTTCGTACCATAAGGCAGTTCATGAGGTATA
TTTCGTTATTGAAGCCCGACTCGTGAATGCTCTAATGCTGTTTCGCTGAACTGGTGTCCATGTCGCCTAGGTACG
CAATCTCCACAGGCTGCAAAGGTTTGTCTCAAGAGCAAATGTTATTGTGCACCCCGTAATTGGTCAACAA
GTTTAATCTGTGCTTGTCCACCAGCTCTGTCAGTTCAACCTTCAGTTCATCGACTATCTGAAGAATTACTA
GGAATAGTGCCATGTACAGCAACGAGAATGGCAATTTCTACTCGGGTTCAGCAACGCTGCATAAACGC
TGTTGGTGCCGTAGACATATTCGAAGATAGGATTATCATTCAGACCAATGTCCTTATTCTG
GAACTTGATTATGCTCTCTTTGGTTTAATTCGCCTGATTCTCCTTTAGCTTCTCGACGTGG
GCCTTTTCTGCCATATGGATCTGAATTCTAGTCTTTTTTGCTGGAACGGTTGAGCGGAAAAGACGCAT
CGAATTCGAGCTCGTTAGCGATTGGCATTATCACATAATGAATTATACATTATATAAAGTAATGTGATTT
CTTCGAAGAATATACTAAAAATGAGCAGGCAAGATAAACGAAGGTATCGATAAGCTTGG
GAATTCAAAATGCCCAAGAAGACGGAAGTCCATATGTACCCATACGACGTTCCAGACTACGCTTCTT
TGGGTGGTTCTAGCCAAGCTTGATATCGAATTCTGCAGCCCGGGATCCTAACATGTCCGTTGCTGA
TGATGATTAGGATCTTTACAAGGTCACATTAGGAGAACACTGAGGTCTATTCATAACCTCCCTATTT
AGGTATACGAGAGTCCTACTGAAAGGGCTGACATGAGCAGAGACTTATTCAATGCTCATCCAAAACAAAATT
TATACTTTGTCATTCTTAACGCGGAGAGAACTTACTTTCCTGACAGTTTAGAAGATGCTGTGATATTGATAAGATAACATCT
ATCTAACCCAGACTATTCCGTTGTTTTATAAGATAGGGAACCCTTGTATAGGTGTCATGAGTGTTGCGATGATACTTG
CAACAAACTATTCATTCATTGTTTTAATCCAAAAGATCATGGTGAATCATGTTTCCTGTGAAATTGTTATCCGCTCACA
ATTGTGGGAGGAAATTCAAAAATAGGGAACCCCTTGTATAGGTGTCATGAGTGTTGCGATGATACTTG
TGTGCTTTGTATTGTTTCATTCATTGTTTTAATCCAAAAGATCATGGTGAATCATGTTTCCTGTGAAATTGTTATCCGCTCACA
GAATTCGATATCAAGCTTGGCGTAATCATGGTCATAGCTGTTTCCTGTGTGAAATTGTTATCCGCTCACA
ATTCCACACAACATACGAGCCGGAAGCATAAAGTGTAAAGCCTGGAGTGAGTGAGCTAACTCA
CATTAATTGCGTTGCGCTCACTGCCCGCTTTCCAGTCGGGAAACCTGTCGTGCCAGCTGCATTAATGAATCGGCCAACGC
TTCTAGAGTCGACCTGCAAGCTTGGCGTAATCATGGTCATAGCTGTTTCCTGTGTGAAATTGTTATGAGTGA
CCGCTCACAATTCCACACAACATACGAGCCGGAAGCATAAAGTGTAAAGCCTGGGGTGCCTAATGAGTGA
GCTAACTCACATTAATTGCGTTGCGCTCACTGCCCGCTTTCCAGTCGGGAAACCTGTCGTGCCAGCTGCA
```

FIG. 5C

```
TTAATGAATCGGCCAACGCGCGGGGAGAGGCGGTTTGCGTATTGGGCGCTCTTCCGCTTCCTCGCTCACT
GACTCGCTGCGCTCGGTCGTTCGGCTGCGGCGAGCGGTATCAGCTCACTCAAAGGCGGTAATACGGTTAT
CCACAGAATCAGGGGATAACGCAGGAAAGAACATGTGAGCAAAAGGCCAGCAAAAGGCCAGGAACCGTAA
AAAGGCCGCGTTGCTGGCGTTTTTCCATAGGCTCCGCCCCCCTGACGAGCATCACAAAAATCGACGCTCA
AGTCAGAGGTGGCGAAACCCGACAGGACTATAAAGATACCAGGCGTTTCCCCCTGGAAGCTCCCTCGTGC
GCTCTCCTGTTCCGACCCTGCCGCTTACCGGATACCTGTCCGCCTTTCTCCCTTCGGGAAGCGTGGCGCT
TTCTCATAGCTCACGCTGTAGGTATCTCAGTTCGGTGTAGGTCGTTCGCTCCAAGCTGGGCTGTGTGCAC
GAACCCCCCGTTCAGCCCGACCGCTGCGCCTTATCCGGTAACTATCGTCTTGAGTCCAACCCGGTAAGAC
ACGACTTATCGCCACTGGCAGCAGCCACTGGTAACAGGATTAGCAGAGCGAGGTATGTAGGCGGTGCTAC
AGAGTTCTTGAAGTGGTGGCCTAACTACGGCTACACTAGAAGGACAGTATTTGGTATCTGCGCTCTGCTG
AAGCCAGTTACCTTCGGAAAAAGAGTTGGTAGCTCTTGATCCGGCAAACAAACCACCGCTGGTAGCGGTG
GTTTTTTTGTTTGCAAGCAGCAGATTACGCGCAGAAAAAAAGGATCTCAAGAAGATCCTTTGATCTTTTC
TACGGGGTCTGACGCTCAGTGGAACGAAAACTCACGTTAAGGGATTTTGGTCATGAGATTATCAAAAGG
ATCTTCACCTAGATCCTTTTAAATTAAAAATGAAGTTTTAAATCAATCTAAAGTATATATGAGTAAACTT
GGTCTGACAGTTACCAATGCTTAATCAGTGAGGCACCTATCTCAGCGATCTGTCTATTTCGTTCATCCAT
AGTTGCCTGACTCCCCGTCGTGTAGATAACTACGATACGGGAGGGCTTACCATCTGGCCCCAGTGCTGCA
ATGATACCGCGAGACCCACGCTCACCGGCTCCAGATTTATCAGCAATAAACCAGCCAGCCGGAAGGGCCG
AGCGCAGAAGTGGTCCTGCAACTTTATCCGCCTCCATCCAGTCTATTAATTGTTGCCGGGAAGCTAGAGT
AAGTAGTTCGCCAGTTAATAGTTTGCGCAACGTTGTTGCCATTGCTACAGGCATCGTGGTGTCACGCTCG
TCGTTTGGTATGGCTTCATTCAGCTCCGGTTCCCAACGATCAAGGCGAGTTACATGATCCCCCATGTTGT
GCAAAAAAGCGGTTAGCTCCTTCGGTCCTCCGATCGTTGTCAGAAGTAAGTTGGCCGCAGTGTTATCACT
CATGGTTATGCAGCACTGCATAATTCTCTTACTGTCATGCCATCCGTAAGATGCTTTTCTGTGACTGGT
GAGTACTCAACCAAGTCATTCTGAGAATAGTGTATGCGGCGACCGAGTTGCTCTTGCCCGGCGTCAATAC
GGGATAATACCGCGCCACATAGCAGAACTTTAAAAGTGCTCATCATTGGAAAACGTTCTTCGGGGCGAAA
ACTCTCAAGGATCTTACCGCTGTTGAGATCCAGTTCGATGTAACCCACTCGTGCACCCAACTGATCTTCA
GCATCTTTTACTTTCACCAGCGTTTCTGGGTGAGCAAAAACAGGAAGGCAAAATGCCGCAAAAAGGGAA
TAAGGGCGACACGGAAATGTTGAATACTCATACTCTTCCTTTTTCAATATTATTGAAGCATTTATCAGGG
TTATTGTCTCATGAGCGGATACATATTTGAATGTATTTAGAAAAATAAACAAATAGGGGTTCCGCGCACA
```

FIG. 5D

```
TTTCCCGAAAAGTGCCACCTGCTAAGAAACCATTATTATCATGACATTAACCTATAAAAATAGGCGTAT
CACGAGGCCAGCTTTTCAATTCATTCATTTTTTATTCTTTTTGATTTCGGTTTCTTTGA
AATTTTTTGATTCGTAATCTCCGAACAGAAGAAGGAGCACAGACTTAGATTGGTAT
ATATACGCATATGTAGTGTTGAAGAAACATGAAAATTGCCCAGTATTCTTAACCAACTGCACAGAACAAA
AACATGCAGGAAACGAAGATAAATCATGTCGAAAGCTACATATATAAGGAACAAACTTGTGTGCTTAGT
CCTGTTGCTGCCAAGCTATTTAATATCATGAAGCACGAAAAGCAAACAAACTTGTGTGCTTCATTGATGTTC
GTACCACCAAGGAATTACTGGAGTTAGTGTTGAAGCATTAGTGCCCAAATTTGTTACTAAAAACACATGT
GGATATCTTGACTGATTTTCCATGGAGGGCACAGTTAAGCCGCTAAAGCATTATCCGCCAAGTACAAT
TTTTACTCTTGAAGACAGAATTGCTGACATTGGTAATACAGTCAAATTGGTGCCCAGTACTCTGCGGGTG
TATACAGAATAGCAGAATATGGGCAGACATTACGAATGCACACGTGGTCCTTTGACATTGCAGTTAGCG
TTTGAAGCAGGCGGCAGAAGAAGTAACAAAGGAACCTAGAGGGTACTGTTGACATTGCGAAGAGCGACAAAGATTTTG
AAGGGCTCCCTATCTGCTTATTGCTCAAAGAGACATGGGTGGAAGATGAAGTTACGATTGGTTGATTATGACACC
CGGTGTGGGTTTAGATGAAGGGAGACGCATTGGGTCAACAGTATAGAACCGTGATGATGGTGCTCT
ACAGGATCTGACATTATTATTGTTGGAAGAGGAAGGATGCTAAGGTAGAGGGTG
AACGTTACAGAAAAGCAGGCATATGAGAAGCATATTTGAGAAGATGCGCCAGCAAAACTAAAAACTGTATT
ATAAGTAAATGCATGTATACTAAACTCACAAATTAGAGCTTCAATTTAATTATATCAGTTATTACCCGCC
CTTTCGTCTCGCGCTTTCGGTGATGACGGGAGCCATGCAGCTCCCGAGACGGTCACA
GCTTGTCTGTAAGCGGATGCCGGGCAGACAAGCCCGTCAGGGCGCGTCAGCGGTGTTGGCGGGTGTC
GGGGCTGGCTTAACTATGCGGCATCATCAGAGAGTGCCATTCAGCCTGTGAATACC
GCACAGATGCGTAAGGAGAAAATACCGCATCAGGCGCATTCGCCGAAAGCTGCGCAACTGTTGGGAA
GGGCGATCGGTGCGGGCCCTCTTCGCTATTACGCCAGCTGGCGAAAGGGGGATGTGCTGCAAGGCGATTAA
GTTGGGTAACGCCAGGGTTTTCCCAGTCACGACGTTGTAAAACGACGGCCAGT
```

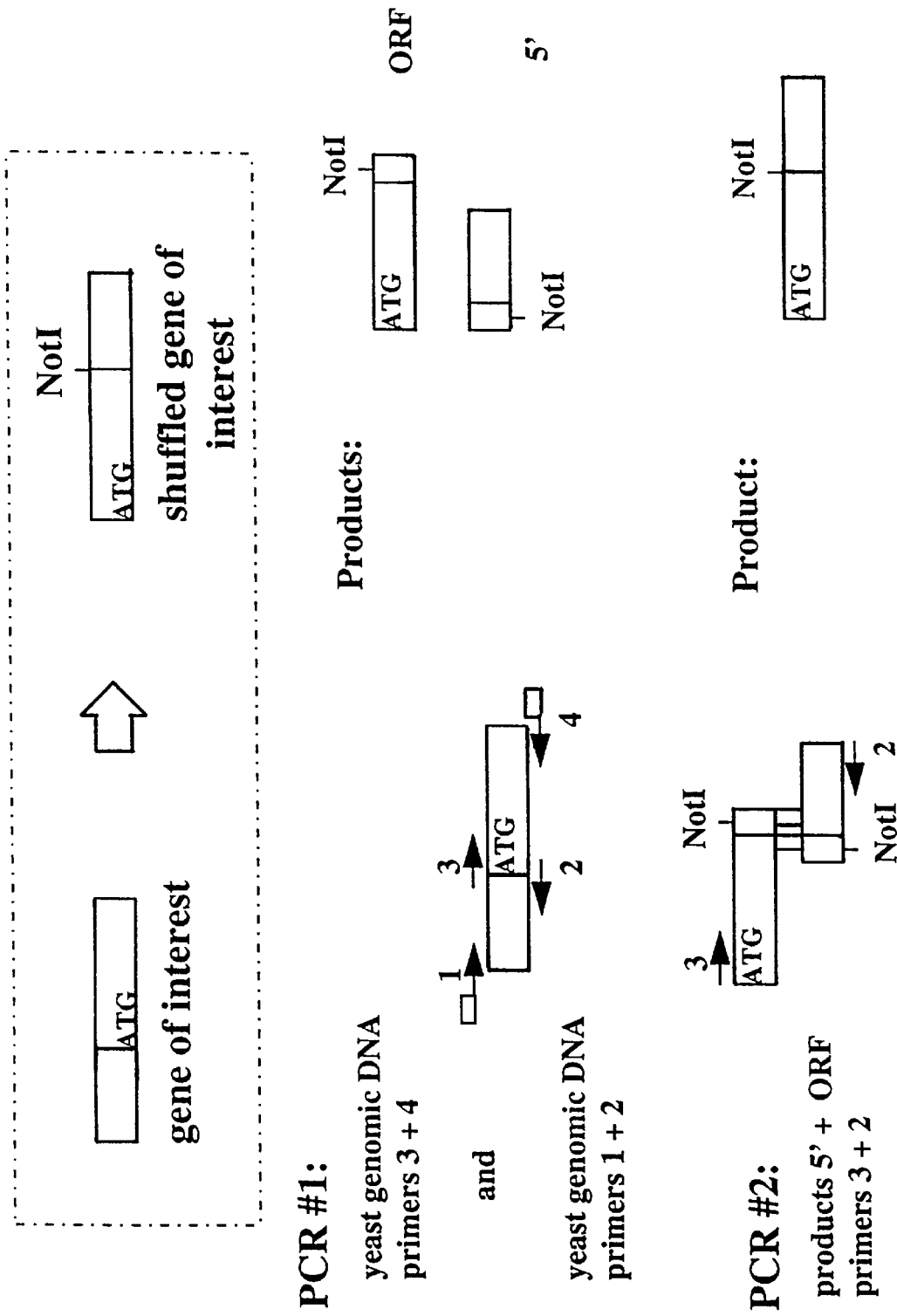

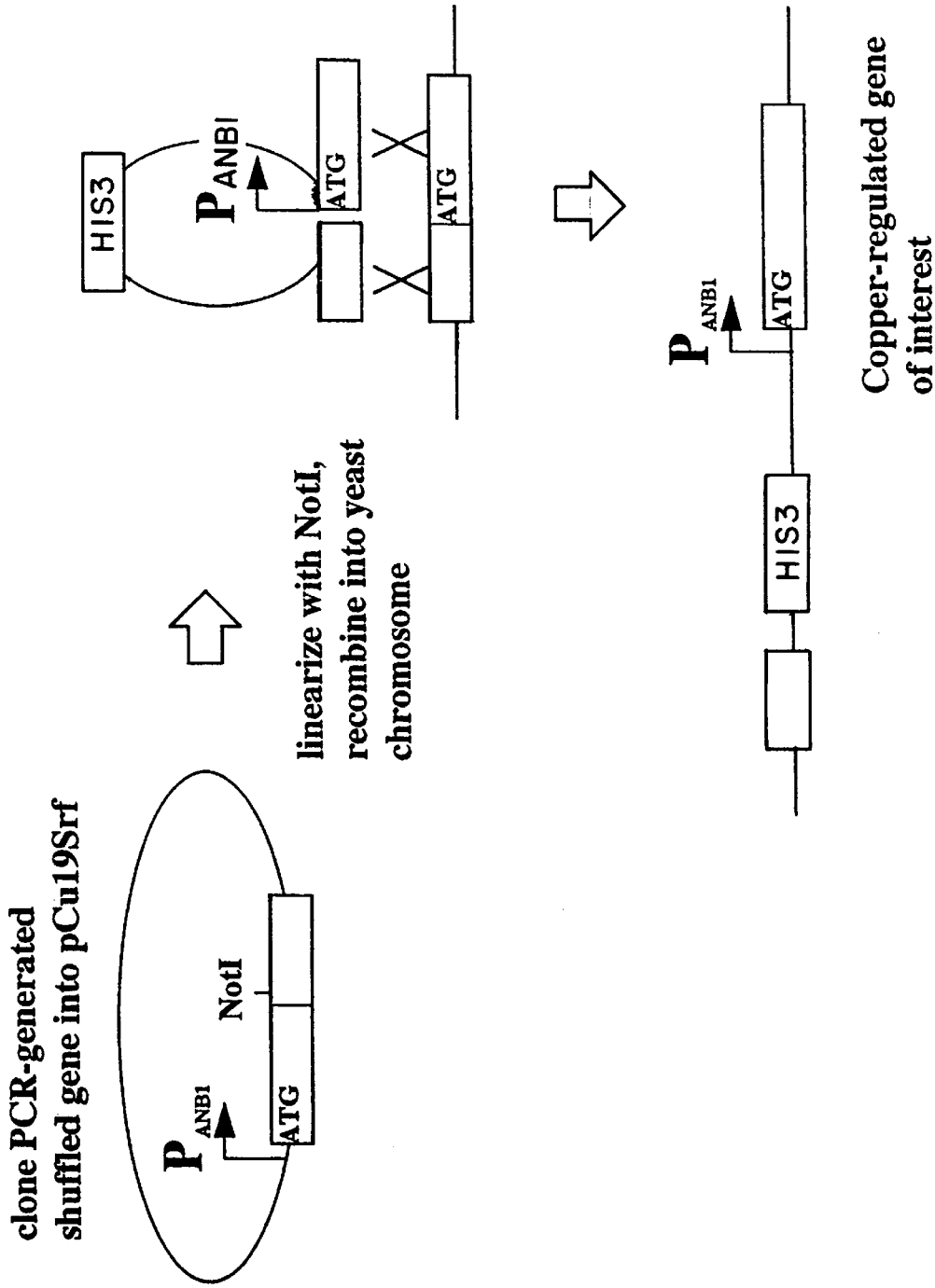

REGULATED GENE EXPRESSION IN YEAST

This application claims priority under 35 U.S.C. § 119(e) from provisional patent application Ser. No. 60/056,719, filed on Aug. 22, 1997, which is hereby incorporated by reference in its entirety.

FIELD OF THE INVENTION

The present invention relates to methods and compositions for regulated expression of specific genes in *Saccharomyces cerevisiae*. The invention can be used to identify and clone genes of interest and to identify antifungal agents using high-throughput screening techniques.

BACKGROUND OF THE INVENTION

The ability to regulate the expression of particular genes of interest is important for many purposes, including, for example, (i) investigation of the biological function of a particular gene product; (ii) design of variants of the gene product that are tailored for different ends; and (iii) identification of agents that influence the activity of the gene product, including, e.g., inhibitors or activators. The ease of performing genetic and molecular manipulations in *S. cerevisiae* has made it an extremely useful experimental organism for regulated expression of recombinant genes. However, many gene expression systems based on *S. cerevisiae* are limited in their applicability by (i) the degree of regulation that can be achieved, i.e., the extent to which genes can be turned on and off, as well as the timing of these events; (ii) the relative stability of certain gene products, which makes it difficult to quickly deplete the cell of a gene product; and (iii) potential metabolic side effects of the procedures used to trigger or initiate changes in gene expression.

Thus, there is a need in the art for *S. cerevisiae* expression systems in which gene expression can be tightly and efficiently regulated, with respect to both transcription of the gene and accumulation of the protein product.

SUMMARY OF THE INVENTION

The present invention encompasses yeast strains in which expression of a particular protein (the "subject" protein) can be tightly regulated. The invention provides *Saccharomyces cerevisiae* cells in which expression of the subject protein can be repressed by exogenous metal. These cells comprise, for example:

(i) a first gene encoding a transcriptional repressor protein, the expression of which has been placed under the control of a metal ion-responsive element, wherein expression of the repressor protein is stimulated by the addition of a metal ion to the growth medium of the cells;

(ii) a second gene encoding a subject protein, wherein expression of the subject protein is controlled by a promoter, the activity of which is inhibited by said repressor protein; and (iii) a third gene encoding a biomineralization protein, wherein the third gene is inactivated and wherein inactivation of the third gene enhances the transcriptional response of the metal-responsive element to added metal ions.

In a preferred embodiment, the first gene is ROX1; the second gene is controlled by an ANB1 promoter; and the third gene is SLF1.

In another embodiment, the yeast cell comprises a fourth gene encoding a protein that targets ubiquitin-containing polypeptides for degradation, where the fourth gene is placed under the control of a metal ion-responsive element. In a preferred embodiment, the fourth gene is the UBR1 gene.

The invention further comprises yeast cells in which expression of the subject protein is stimulated by exogenous metal ions. These cells comprise:

(i) a first gene encoding a subject protein, wherein expression of the gene encoding the subject protein is under the control of a metal ion-responsive element and is stimulated by the addition of a metal ion to the growth medium of the cells; and (ii) a second gene encoding a biomineralization protein, wherein the second gene is inactivated and wherein inactivation of the second gene enhances the transcriptional response of the metal-responsive element to added metal ions.

In a preferred embodiment, the metal-responsive element is the Sc3451 promoter and the second gene is SLF1.

In another aspect, the invention relates to a method for the introduction of a subject gene under the control a predetermined promoter DNA sequence into a yeast cell genome, comprising the steps of providing a shuffled gene fragment, where the fragment comprises a restriction enzyme cleavage sequence, ligating the shuffled gene fragment into a vector, where the ligation results in the shuffled gene fragment being operably linked to a predetermined transcriptional control DNA sequence, cutting the vector with a restriction enzyme specific for the restriction enzyme cleavage sequence to yield a linearized vector, and transforming a yeast cell with the linearized vector.

The invention also provides methods for repressing or activating expression of a gene encoding a subject protein in *S. cerevisiae* to a predetermined level, comprising culturing the strains described above in the presence of metal, wherein the metal is present at sufficient concentration to activate the metal-responsive element so as to achieve the predetermined level of repression or activation of the gene.

BRIEF DESCRIPTION OF THE DRAWINGS

FIG. 4 is an illustration of the nucleotide sequence of the ZM195 plasmid (SEQ ID NO:20).

FIG. 5 is an illustration of the nucleotide sequence of the ZM197 plasmid (SEQ ID NO:21).

FIG. 6 is a schematic illustration of the PCR strategy used to generate shuffled genes for transformation into S. Cerevisiae.

FIG. 7 is a schematic illustration of the transformation mechanism by which shuffled genes are introduced into S. cerevisiae.

DETAILED DESCRIPTION OF THE INVENTION

Figure 1:
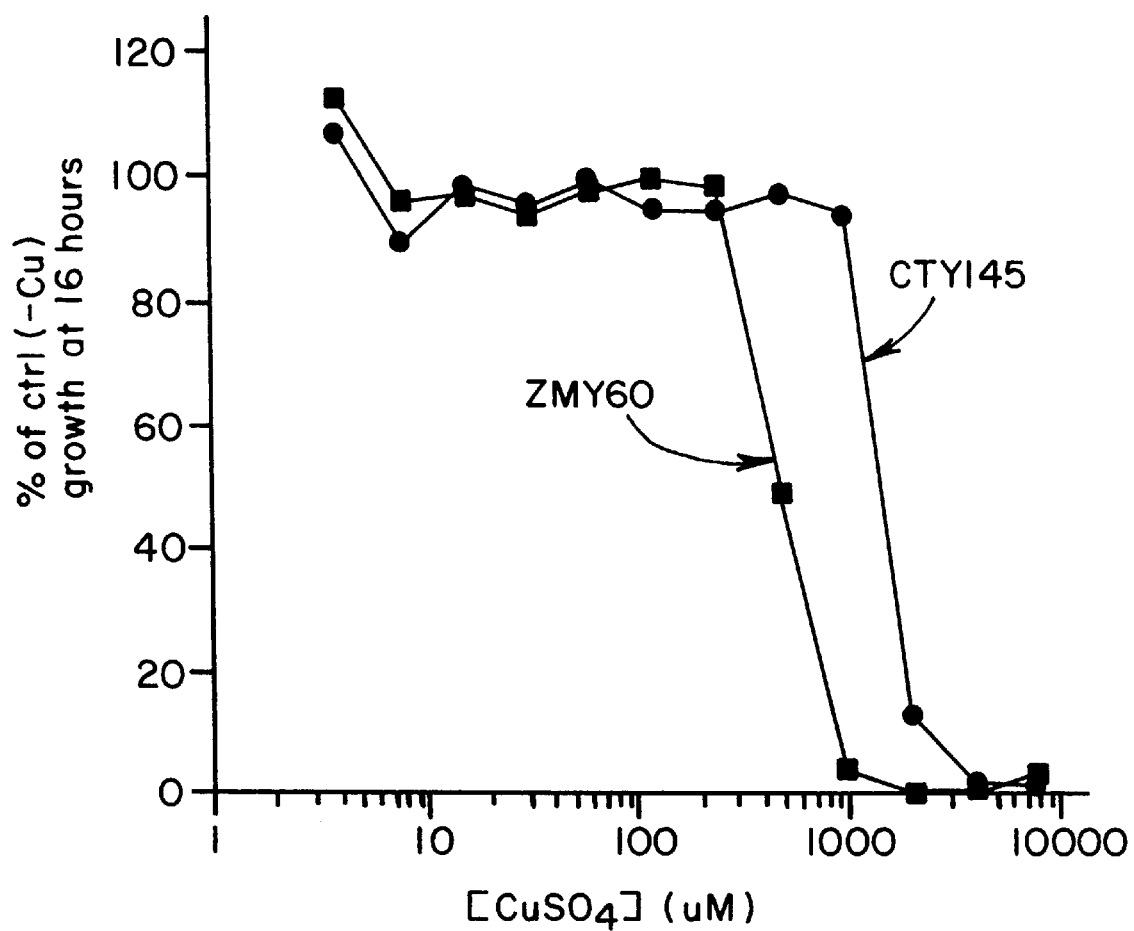
FIG. 1 is a graphic illustration of the growth of yeast strains CTY145 and ZMY60 in increasing concentrations of copper sulfate. CTY145 is four-fold more tolerant to copper than ZMY60.

All patents, patent applications, publications and other materials cited herein are hereby incorporated by reference in their entirety. In the case of inconsistencies, the present description, including definitions, is intended to control.

As used herein, the term "transcriptional repressor protein" refers to a protein which either binds directly to a transcriptional control sequence or which binds in association with other proteins or cofactors to a transcriptional control sequence, resulting in the repression of transcription of the protein encoding nucleotide sequence or sequences to which the transcriptional control sequence is operably linked.

As used herein, the term "transcriptional control sequence" refers to DNA sequences, such as initiator sequences, enhancer sequences, and promoter sequences, which induce, repress, or otherwise control the transcription of protein encoding nucleic acid sequences to which they are operably linked.

As used herein, the term "metal-ion responsive element" refers to a transcriptional control sequence which is activated when in the presence of an appropriate concentration of metal ions.

As used herein, the term "inactivated", when referring to a gene, means that the gene cannot be transcribed, either due to deletion of the gene from a genome or by disruption of its coding or regulatory sequences.

As used herein, the term "biomineralization protein" refers to a protein that promotes or catalyzes the conversion of ionic copper to a form insoluble in water, such as CuS.

As used herein, the term "shuffled gene fragment" refers to the nucleotide sequence around the ATG initiation codon of a gene, from about 400 nucleotides upstream of (i.e., 5' to) the ATG initiation codon of the gene to about 400 protein coding nucleotides downstream of (i.e., 3' to) the ATG initiation codon of the gene, wherein the orientation of the upstream and downstream sequences have been changed such that the ATG initiation codon and the approximately 400 downstream protein coding nucleotides that follow the ATG codon in the wild-type gene are upstream to the approximately 400 noncoding nucleotides normally found adjacent and upstream of the ATG initiation codon. The shuffled gene fragment will typically contain a restriction enzyme cleavage sequence between the rearranged coding and noncoding nucleotide sequences.

As used herein, the term "restriction enzyme cleavage sequence" refers to a specific nucleotide sequence which is specifically recognized and cleaved by one or more restriction endonuclease enzymes.

As used herein, the term "operably linked" refers to the covalent attachment, typically of a transcriptional control sequence to a protein encoding nucleotide sequence, such that transcription of the protein encoding nucleotide sequence is regulated or controlled by the transcriptional control sequence.

As used herein, the term "linearized vector" refers to the cleavage product of circular double stranded DNA molecule, or vector, which has been cleaved at a single site, yielding a linear double stranded DNA molecule.

The present invention encompasses methods and compositions for regulating the expression of a gene of interest in Saccharomyces cerevisiae. The invention provides recombinant yeast strains which comprise:

(i) a gene encoding a transcriptional repressor protein, the expression of which gene has been placed under the control of a metal ion-responsive element, so that expression of the gene encoding the repressor protein is stimulated by the addition of a metal ion to the growth medium of the cells;

(ii) a gene encoding a protein of interest, the expression of which gene is inhibited by the repressor protein described in (i); and (iii) one or more genes involved in metal ion metabolism that have either been inactivated or overexpressed, depending on the gene, to enhance the transcriptional response to added metal ion.

In the above yeast cells (a large number of such clonal cells being collectively designated "repressing strains"), the gene of interest is expressed in the absence of added metal ion. When it is desired to decrease or eliminate expression of the gene of interest, metal ions are added to the medium, which stimulates expression of the repressor to a degree that is dependent upon the concentration of added metal ions and represses transcription of the gene of interest.

The invention also encompasses yeast cells (a large number of such clonal cells being collectively designated "inducing strains") in which: (i) the gene of interest is operably linked to a metal ion-inducible transcriptional control sequence, so that expression of the gene of interest is directly stimulated by addition of metal ions to the medium; and (ii) one or more genes involved in metal ion metabolism that have either been inactivated or overexpressed, depending on the gene, to enhance the transcriptional response to added metal ion.

The choice of yeast strain in which the above manipulations are performed is important in practicing the invention. Suitable strains are those that tolerate the addition of metal ions to their culture medium at a sufficient concentration, and for a sufficient time period, to allow maximal expression of metal-inducible genes while maintaining cell viability and metabolism. Preferably, the growth rate of the strain should remain substantially unaffected for at least about 16 h after the addition of at least 750 $\mu$M copper sulfate, most preferably at least 1 mM copper sulfate. In addition, the strain should grow well and should be auxotrophic for common nutrients such as histidine, leucine, and uracil, to enable the use of, e.g., HIS3, LEU2, and URA3 as markers for genetic insertions. Suitable yeast strains include without limitation CTY145 and S288C (ATCC #26108).

In some embodiments, the repressing strains of the invention further comprise a gene encoding a protein that targets ubiquitin-containing polypeptides for degradation via the ubiquitin degradation pathway, which, similar to the repressor gene, is expressed under the control of a metal ion-responsive regulatory element. In these embodiments, the gene of interest is expressed as a fusion protein, which contains at its amino terminus additional amino acids comprising a sequence that targets the polypeptide for the ubiquitin degradation pathway. In this manner, addition of metal ions to the medium also stimulates degradation of the protein of interest by the ubiquitin pathway, thereby depleting the protein from the cell. It will be understood, however, that some proteins of interest cannot be expressed in functional form as ubiquitin-targetable fusion proteins. Furthermore, overexpression of a ubiquitin-pathway gene may exert pleiotropic and potentially deleterious effects. Accordingly, the invention also encompasses repressing strains that do not overexpress a ubiquitin pathway protein and in which the gene of interest is not expressed as a fusion protein.

In practicing the invention, any metal ion-responsive transcriptional control element may be used, including without limitation DNA sequences comprising the binding site for the ACE1 protein, which has been identified as the sequence spanning nucleotides −105 to −148 of the CUP1 (metallothionein) promoter (Huitbregtse et al., *Proc. Natl. Acad. Sci. USA* 86: 65, 1989). Metal ion-responsive elements may be used singly or in tandem repeats, in direct or reverse orientation relative to a transcription start site, and may be combined with any compatible promoter such as, e.g., the HIS3 promoter. In conjunction with these elements, any suitable metal ion may be used to stimulate expression, including without limitation Ag, Cu, Cd, Ni, Zn, and Fe ions. Suitable repressor proteins for use in the invention include without limitation ROX1, a heme-induced repressor of hypoxic genes (Genbank accession number #X60458) (Deckert et al., *Genetics* 139: 1149, 1995), LexA-CYC8 fusion proteins and LexA-TUP1 fusion proteins (Redd et al., *Cell* 78: 709, 1992). It will be understood that the choice of promoter sequences to be placed upstream of the gene of interest will be determined by the particular repressor used. For example, when ROX1 is the repressor, the promoters directing expression of the gene of interest may be derived from, e.g., the ANB1, HEM13, ERG11, or OLE1 genes. The sequences of these genes are disclosed under the following Genbank accession numbers: #M23440 (ANB1); #S81592 (HEM13); #U10555, U00093 (ERG11); and #U42698, #J05676 (OLE1). When the repressor contains bacterial LexA domains, the promoters directing the expression of the gene of interest may comprise sequences derived from the LexA operator. The sequence of the LexA operator is 5'-TACTGATGTACATACAGTA-3' (Tzamarias et al., *Nature* 369: 758, 1994) (SEQ ID NO:1); a synthetic LexA operator may also be employed, comprising the sequence: 5'-TCGAGTACTGTATGTACATACAGTACCATGACA-TACATGTATGTCATGAGCT-3' (U.S. Pat. No. 4,833,080) (SEQ ID NO:2).

The genes involved in metal ion metabolism that may be inactivated to form the yeast strains of the present invention include without limitation SLF1, which is involved in the biomineralization pathway of copper (Genbank accession number U30375) (Yu et al., *Mol. Cell. Biol.* 16: 2464, 1996). In the case of SLF1, inactivation of the gene slows the depletion of copper from the growth medium and thereby enhances the transcriptional response of the repressor-encoding gene to the added copper ions. The result is an increase in the time period in which a consistent copper regulation of gene expression can be maintained. Alternatively, genes encoding proteins such as, e.g., CTR1 (a metal ion transporter) can be overexpressed to increase the sensitivity of the transcriptional apparatus to the added metal ion (Dancis et al., *J Biol. Chem.* 269: 25660, 1994).

In the embodiments in which a ubiquitin-pathway protein is expressed under metal ion control, any ubiquitin-pathway protein may be expressed that will stimulate the degradation of an appropriately amino terminal tagged protein of interest. In one embodiment, the ubiquitin pathway protein that is linked to a metal ion-responsive element is UBR1 and the amino terminal tag is a hybrid sequence comprising, in amino terminal-to-carboxyl terminal direction, ubiquitin and a 31-amino acid segment of the lac repressor protein (LacI), and may additionally include one or more epitope tags (Park et al., *Proc. Natl. Acad. Sci. USA* 89: 1249, 1992). In this embodiment, the hybrid protein (containing at its carboxyl terminus the protein of interest) is rapidly de-ubiquinated by yeast enzymes, and the resulting hybrid protein (containing an arginine residue at its amino terminus) is re-ubiquinated by the UBR1 protein (in the presence of a metal ion) and targeted for degradation.

Moqtaderi et. al., *Nature* 383: 188,1996, disclose a haploid yeast strain (ZMY60) carrying integrated copies of the ROX1 and UBR1 genes which were placed under the control of the ACE1 promoter. Into this genetic background, a plasmid containing the ANB1 promoter driving expression of an in-frame fusion of ubiquitin, arginine, lacI, hemagglutinin epitopes and the full length gene of interest was introduced. Addition of 500 $\mu$M cupric sulfate (CuSO$_4$) to the medium resulted in the repression of transcription of the gene of interest by ROX1 and rapid degradation of the ubiquitin-tagged protein. However, this strain is relatively genetically unstable resulting in frequent reversion to a copper-insensitive phenotype, is highly sensitive to the toxic effects of copper ions at concentrations above 250 $\mu$M, and responds to copper ions for a relatively short time (in part, due to depletion of copper ions from the medium by biomineralization). The yeast strains of the present invention, by contrast, tolerate concentrations of copper ions of 1 mM or greater for extended periods of time. Furthermore, the yeast strains of the present invention exhibit more stable phenotypes, due to the use of methods which employ double-crossover events for integration of engineered genes into the yeast genome (see, e.g., Examples 3 and 4 below).

In one set of embodiments, the invention provides a CTY145-based yeast strain in which: (i) the native ROX1 gene promoter has been replaced with a promoter comprising a hybrid HIS3 promoter-ACE1 binding site; (ii) the native SLF1 gene has been deleted; and (iii) the gene of interest is controlled by an ANB1 promoter. Features (i)–(iii) are preferably achieved using a double-crossover strategy. In an alternate embodiment, the CTY145 strain has been modified as in (i) and (ii) above, and, in addition, (iii) the native UBR1 gene promoter has been replaced with a promoter comprising a hybrid HIS3 promoter-ACE1 binding site; and (iv) a sequence which comprises an ANB1 promoter followed by a sequence encoding a hybrid polypeptide comprising ubiquitin, a LacI fragment, and an epitope tag is fused to the 5' end of the protein-coding sequence of a gene of interest.

In another set of embodiments, the invention provides a CTY145-based yeast strain in which: (i) a gene has been introduced comprising a hybrid HIS3 promoter-ACE1 binding site placed upstream of sequences encoding a CYC8-

LexA fusion protein; (ii) the native SLF1 gene has been deleted; and (iii) a gene of interest is controlled by a promoter comprising a LexA operator. Features (i)–(iii) are preferably achieved using a double-crossover strategy. In an alternate embodiment, the CTY145 strain has been modified as in (i) and (ii) above, and, in addition, (iii) the native UBR1 gene promoter has been replaced with a promoter comprising a hybrid HIS3 promoter-ACE1 binding site; and (iv) a sequence which comprises a LexA operator-containing promoter followed by a sequence encoding a hybrid polypeptide comprising ubiquitin, a LacI fragment, and an epitope tag is fused to the 5' end of the protein-coding sequence of a gene of interest.

In another set of embodiments, the invention provides a CTY145-based yeast strain in which (i) the gene of interest is controlled by the Sc3451 promoter and (ii) the native SLF1 gene has been deleted. The Sc3451 promoter was constructed by cloning an ACE1 binding site (5'-TAAG-TCTTTTTTGCTGGAACGGTTGAGCGGAAAAGAC-GCATC-3') (SEQ ID NO:3) upstream of the TATAA sequence at an EcoRI site in plasmid YIp55-Sc3370 (Struhl et al., *Mol. Cell Biol* 7: 104, 1987).

METHODS

In practicing the present invention, many conventional techniques in molecular biology, microbiology, and recombinant DNA, are used. Such techniques are well known and are explained fully in, for example, *Current Protocols in Molecular Biology*, Volumes I, II, and III, 1997 (F. M. Ausubel ed.); Sambrook et al., 1989, *Molecular Cloning: A Laboratory Manual*, Second Edition, Cold Spring Harbor Laboratory Press, Cold Spring Harbor, N.Y.; *DNA Cloning: A Practical Approach*, Volumes I and II, 1985 (D. N. Glover ed.); *Oligonucleotide Synthesis*, 1984, (M. L. Gait ed.); *Nucleic Acid Hybridization*, 1985, (Hames and Higgins); *Transcription and Translation*, 1984 (Hames and Higgins eds.); *Animal Cell Culture*, 1986 (R. I. Freshney ed.); *Immobilized Cells and Enzymes*, 1986 (IRL Press); Perbal, 1984, *A Practical Guide to Molecular Cloning;* the series, *Methods in Enzymology* (Academic Press, Inc.); and *Methods in Enzymology* Vol. 154 and Vol. 155 (Wu and Grossman, and Wu, eds., respectively).

Insertion of nucleic acids (typically DNAs) comprising the sequences of the present invention into a vector is easily accomplished when the termini of both the DNAs and the vector comprise compatible restriction sites. If this cannot be done, it may be necessary to modify the termini of the DNAs and/or vector by digesting back single-stranded DNA overhangs generated by restriction endonuclease cleavage to produce blunt ends, or to achieve the same result by filling in the single-stranded termini with an appropriate DNA polymerase.

Alternatively, any site desired may be produced, e.g., by ligating nucleotide sequences (linkers) onto the termini. Such linkers may comprise specific oligonucleotide sequences that define desired restriction sites. Restriction sites can also be generated by the use of the polymerase chain reaction (PCR). See, e.g., Saiki et al., 1988, *Science* 239: 48. The cleaved vector and the DNA fragments may also be modified if required by homopolymeric tailing.

The nucleic acids may be isolated directly from cells. Alternatively, the polymerase chain reaction (PCR) method can be used to produce the nucleic acids of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

Methods for yeast transformation, integration of genes into the yeast genome, and growth and selection of yeast strains are fully described in, e.g., *Current Protocols in Molecular Biology*, Vols. 1 and 2, Ausubel et al., eds., John Wiley & Sons, New York (1997). The use of URA3 for the production of multiply disrupted yeast strains is disclosed in Alani et al., *Genetics* 116: 541, 1987.

A preferred method for the transformation of *S. cerevisiae* is as follows. Yeast strains are cultured overnight in YPD (yeast extract, peptone, dextrose) medium at about 30° C. The resulting culture is diluted to an $A_{600}$ of about 0.2 in about 200 ml YPD medium and incubated at about 30° C. until the $A_{600}$ reaches approximately 0.8. The cells are pelleted by centrifugation and are washed in about 20 ml sterile water. The pelleted yeast cells are then resuspended in about 10 ml TEL (10mMTris pH7.5, 1 mM EDTA, 0.1 M LiAcetate pH 7.5) buffer. The cells are pelleted by centrifugation and again resuspended in about 2 ml TEL. About 100 μg of well-sheared single stranded DNA and plasmid DNA are added to an eppendorf tube. To this tube is added about 100 μl of competent yeast cells, followed by mixing. To the cell/DNA mixture is added about 0.8 ml of 40% PEG-3350 in TEL, followed by thorough mixing. This mixture is incubated for about 30 minutes at 30° C., followed by a heat shock for 20 minutes at 42° C. The mixture is centrifuged to remove the supernatant and pellet the cells. The yeast cell pellet is washed with about 1 ml TE, pelleted again by centrifugation, and then plated on selective media.

A preferred method for the extraction of genomic DNA from *S. cerevisiae* for PCR is as follows. A 5 ml overnight yeast strain culture grown in YPD at 30° C is spun out by centifugation and washed once in 1 ml Tris pH 7.5/1 mM EDTA (TE) buffer. The cells are pelleted again by centrifugation and resuspended in 0.2 ml Extraction Buffer (2% Triton X100, 1% SDS, 100 mM NaCl, 10 mM Tris pH 7.5 and 1 mM EDTA) plus 0.2 ml phenol/chloroform/isoamyl alcohol. About 0.3 g of acid washed glass beads are added. This mixture is vortexed (i.e., agitated vigorously) for 30 minutes. 0.2 ml TE buffer is then added. The mixture is centrifuged and the aqueous phase is removed. The DNA is precipitated from the aqueous phase with two volumes of ethanol. The precipitate is pelleted by microcentrifugation, and resuspended in 50 μl TE plus 5 μg/ml RnaseA enzyme. The resulting preparation can be diluted to a desired concentration, or used directly for PCR reactions.

For assaying the effects of copper ions on recombinant yeast strains, wild type and recombinant strains are grown in 5 ml of CSM media on a roller drum incubation apparatus at 30° C. for 18 to 20 hours. Cultures are diluted to an $A_{600}$ (absorbance of light at 600 nm) of about 0.02 in 5 ml CSM media without or with various concentrations of $CuSO_4$ (10 μM, 50 μM, 100 μM, 250 μM, 1 mM and 2 mM) for 18 to 20 hours. The $A_{600}$ of the various samples is read and recorded.

Yeast strains are tested by a time course in the presence and absence of copper to determine if the depletion of target gene product is fungistatic (i.e., inhibitory to growth)or fungicidal (i.e.,yeast killing). Cultures are started from a single yeast colony in CSM media (5 ml) and grown at 30° C. for 18–20 hours in a roller drum. Cultures are diluted in fresh media to a final volume of 10 ml at an $A_{600}$ of about 0.25 and allowed to grow at 30° C. for 1 hour. The cultures are split into two aliquots and 1 mM $CuSO_4$ is added to one of the aliquots. A sample of 300 μl is immediately taken from each culture aliquot as the zero time point. Other similar samples are taken at 1, 3, 5, 7 and 24 hours after $CuSO_4$ addition. Alternatively, the cultures can be diluted to an $A_{600}$ of about 0.1 and allowed to grow for 3 hours, at which time the cultures are diluted again to an $A_{600}$ of about 0.02, after which 1 mM $CuSO_4$ is added. To measure the absorbance of a yeast culture, typically two-hundred microliters of each sample is taken and added to a 96-well flat bottom polystyrene plate, which is then inserted into a plate reader where the absorbance at 595 nm is measured. A growth curve can be generated from these readings.

When plating cells on YPD medium for analysis of CFU number, typically 100 μl of each sample is serially diluted in 900 μl sterile water. Plating dilutions for yeast cultured without copper ions and for wild type yeast cultured in the presence of copper ions are from $10^{-3}$ to $10^{-6}$. Plating dilutions for time points 0, 1, 3, 5, and 7 hrs for recombinant yeast cultured in the presence of copper ions range from $10^{-2}$ to $10^{-5}$. Plating dilutions for any 24 hour time points for yeast cultured in the presence of copper ions ranges from undiluted to $10^{-2}$.

Typically, about one-hundred microliters of each dilution is plated on YPD agar plates and incubated at 30° C for 48 hrs. Colonies are counted and recorded. Calculations are made to convert colony counts to CFU/ml of original culture medium.

Applications

The yeast strains of the present invention find use for:

(i) Rapid and efficient determination of whether a particular gene of interest can serve as a potential target for discovery of antifungal drugs. This is achieved by assessing whether the rapid depletion from yeast cells of a particular gene product (using the "repressing strains" described above) leads to slowing of cell growth or cell death. Since the most effective drugs are those whose effect is rapidly fungicidal, a gene product whose depletion leads to cell death would be a potential target for antifungal drugs. Because the degree of the reduction in the amount of the gene product can be controlled by the concentration of metal added, it is further possible to determine the degree of reduction of the gene product necessary to cause cell death.

(ii) Identification of target gene products whose rapid depletion leads to increased sensitivity to known antifungal drugs. This phenomenon could also identify potential synergies between known drugs and newly discovered antifungal compounds (see below).

(iii) Rapid cloning of functionally complementary genes from other organisms, including pathogenic fungi such as *C. albicans* and *A. fumigatus*.

(iii) Development of libraries of strains, each of which contains a different gene which is either positively or negatively regulated by copper. Such libraries are useful for identifying targets for antifungal drugs whose mechanism of action is unknown. For example, if stimulation or repression of expression of a particular gene leads to decreased and increased sensitivity, respectively, to a particular drug, then the gene is likely to be involved in mediating the in vivo action of the drug.

(iv) Development of high-throughput screening methodologies to detect antifungal compounds. Such compounds may be found in, for example, natural product libraries, fermentation libraries (encompassing plants and microorganisms), combinatorial libraries, compound files, and synthetic compound libraries. For example, synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich Chemical Company, Inc. (Milwaukee, Wis.). Alternatively, libraries of natural compounds in the form of bacterial, fungal, plant and animal extracts are available from, for example, Pan Laboratories (Bothell, Wash.) or MycoSearch (NC), or are readily producible. Additionally, natural and synthetically produced libraries and compounds are readily modified through conventional chemical, physical, and biochemical means (Blondelle et al., *TibTech* 14: 60, 1996).

The following examples are intended as non-limiting illustrations of the present invention.

EXAMPLE 1

Construction of a Copper-Tolerant Yeast Strain Containing a Copper-Regulated ROX1 Gene The following experiments were performed to: (i) examine the copper sensitivity of different yeast strains; and, (ii) to create a copper-dependent yeast strain containing a copper-regulatable ROX1 gene.

The copper sensitivity of yeast strain CTY145 was compared with that of ZMY60 by growing each strain in the presence of increasing amounts of added copper and measuring cell number at increasing times. After 16 hours of growth, the highest concentration of copper at which the log-phase growth rate of ZMY60 was maintained unaffected was 250 μM. (FIG. 1). By contrast, the highest concentration of copper at which the growth rate of CTY145 was maintained was 1 mM. Thus, CTY145 is at least four-fold more tolerant to copper than ZMY60.

A strain based on CTY145 that contains a copper inducible ROX1 was constructed as follows. Using a conventional lithium acetate/polyethylene glycol technique, CTY145 was transformed with approximately 0.1 μg of plasmid pZM195 (FIG. 4), which was linearized with the restriction enzyme AflII. The plasmid contains a metal responsive element comprising HIS3 promoter sequences fused to ACE1.

Integration of the plasmid into the genome was monitored by the ability of the cells to grow on -URA plates (growth of the yeast strains in this medium requires the functional URA3 gene contained on the plasmid). After 48 hours at 30° C., the transformants were inoculated onto fresh -URA plates and regrown for an additional 48 hours at 30° C. Well spaced individual colonies were picked and inoculated to 5 ml YPD media, grown overnight at 30° C., and 5 μl of the culture was inoculated into 5-FOA plates. In the presence of a functional URA3 gene, 5-FOA is converted to a toxin which kills cells. Therefore, the only cells that survive are those that have lost the URA3 gene by recombination.

Integration of ZM195 into the genome could occur in any of the following ways: (1) The original integration could occur non-specifically. In this case, the 5-FOA-induced deletion of URA3 would have no effect. (2) The original incorporation could occur specifically, and the subsequent 5-FOA induced deletion would result in a return to the original promoter sequence. (3) The original integration could occur specifically, and the subsequent 5-FOA induced deletion of URA3 could lead to the correct insertion of the copper-inducible promoter directly upstream of the ROX1 open-reading frame (ORF).

To detect the correct promoter insertion, three PCR primers were designed: ROX-A (5'-TCACACAAAAGAACGCAG-3') (SEQ ID NO:4), corresponding to a sequence from the region of the original promoter immediately 5' to the first ATG of the ORF; ROX-B (5'-GATGACAGCTGTGGTAGG-3') (SEQ ID NO:5), the reverse complement of a sequence in the ORF of ROX1 which is not present in ZM195; and ROX-C (5'-TCTTGCCATATGGATCTG-3') (SEQ ID NO:6), a sequence internal to the copper inducible promoter. For possibilities 1 and 2 above, PCR amplification of genomic DNA with ROX-A and ROX-B would lead to a 601 base pair (bp) product, and PCR amplification with ROX-B and ROX-C would yield no product. For possibility 3, the correct insertion, PCR using ROX-A and ROX-B would yield a 2628 bp product, and PCR with ROX-B and ROX-C would yield a 785 bp product. PCR analysis identified a strain that had undergone the correct rearrangements. This strain was designated CUY 101.

To bring the UBR1 gene under the control of the copper inducible promoter, HIS3-ACE1, the above-described procedure was repeated using CUY101 as the starting strain. The ZM 197 plasmid (FIG. 5) that had been linearized by digestion with the restriction enzyme AatII was introduced into the cells. To identify cells in which the correct promoter insertion had occurred, three PCR test primers were designed: UBR-A (5'-ATCTTCGGACAAAGGCAG-3') (SEQ ID NO: 7); UBR-B (5'-GTGTAATTTTCGGGATCG-3') (SEQ ID NO:8) and ROX-C (5'-TCTTGCCATATGGATCTG-3') (SEQ ID NO:9). PCR analysis is used to identify one culture which has undergone the correct rearrangements. This strain is designated CUY103.

EXAMPLE 2
Construction of a Yeast Strain Containing A Deletion of SLF1

In practicing the present invention, it is preferred that copper regulation of expression be maintained over a relatively long time period, i.e., for several days. The transient effect of copper in wildtype yeast is due at least in part to the fact that yeast cells are able to biomineralize copper. Thus, over time wild-type yeast cells deplete the medium of copper and the effect on expression is lost. If biomineralization activity is ablated, then the extracellular copper levels should remain nearly constant over time.

The only known gene in the yeast copper ion biomineralization pathway is the SLF1gene. Inactivation of the SLF1 gene has been shown to result in cells which are slightly more sensitive to copper but are unable to efficiently deplete copper from the media (Yu et al., *Mol. Cell Biol.* 16: 2464, 1996). Therefore, the SLF1 gene in the yeast strains described in Example 1 above was inactivated.

A construct was created for a two-step knockout of the SLF1 open reading frame. Primers SLF-E (5'-GCGCTGCAGGTCGACTTAGCAGGCAGTTTGAAC-3') (SEQ ID NO: 10) and SLF-F (5'-GCGCTGCAGGCATGCACTCCTTTCCAATTGTGC-3') (SEQ ID NO: 11) were used to amplify the 3'- untranslated region of SLF1 using genomic DNA as template. The SalI/SphI fragment of the PCR product was subcloned into SalI/SphI-digested pUC19 plasmid (Genbank accession no. M77789). This recombinant plasmid was designated pSLF3'. Similarly, primers SLF-G (5'-GCGAGCTCGGTACCCCATACCCCTAACTCTAG-3') (SEQ ID NO: 12) and SLF-H (5'-GCGGATCCCGGGGCTCTCTCGTTTATTTAACG-3') (SEQ ID NO: 13) were used to amplify the 5'- untranslated region of SLF1, and the SacI/BamHI or KpnI/BamHI fragment was cloned into SacI/BamHI or KpnI/BamHI digested pSLF3' to produce pSLF3'5'. The 5.5 kb BamHI/XbaI insert of pDJ20, which contains the yeast URA3 gene and bacterial kanamycin resistance gene flanked by a direct repeat of the Salmonella HisG sequence, was subcloned into XbaI/BamHI digested pSLF3'5' to create pSLFKO. Plasmid pDJ20 is derived from the plasmid pSP72 (Promega, Madison, Wis.) into the BamHI site of which has been cloned the approximately 5.5. kb insert consisting of the following elements:

|hisG|URA3|kanamycin resistance|hisG|

The hisG elements are present as a tandem repeat. Plasmids containing this element can be transformed into bacteria for amplification; selection with kanamycin helps to avoid unwanted recombination between the two hisG regions in bacteria which would result in the loss of the *S. cerevisiae* URA3 gene. The hisG, URA3 and kanamycin genes are well-known in the art and can be assembled in this order by conventional techniques in molecular biology, and do not need to be obtained from plasmid pDJ20.

This plasmid (pSLFKO) was digested with SphI and EcoRI and transformed into strains ZMY60, CTY145, CUY101, and CUY103 using a conventional lithium acetate/polyethylene glycol technique, as described above in the Methods section. Integration of the plasmid into the genome of each yeast strain was monitored by the ability of the strain to grow on (-)URA plates. After 48 hours at 30° C., the transformants were inoculated onto fresh (-)URA plates and regrown for an additional 48 hours at 30° C. Well spaced individual colonies were inoculated into 5 ml YPD media, grown overnight at 30° C., and 5 µl of the culture was inoculated onto 5-FOA plates.

In the presence of a functional URA3 gene, 5-FOA is converted to a toxin which kills cells. Therefore, the only cells that survive are those which have lost the URA3 gene by recombination. Either of the following could occur: (1) Non-specific integration of the linear DNA containing the 5'-HisG-URA3-kanR-HisG-3'NTS fragment could occur, followed by deletion of the region between the HisG repeats; this would result in a 5'NTS-HisG-3'NTS integration at some random spot. (2) Alternatively, specific integration of the linear DNA containing the 5'NTS-HisG-URA3-kanR-HisG-3'NTS sequence could occur, followed by deletion, which would result in a deletion/insertion in which the entire ORF of SLF1 has been deleted and a single copy of the HisG element has been left in its place.

To confirm that the correct genetic alteration occurred, PCR was performed using the following sets of primers: (i) HISGCH (5'-GATTTGGTCTCTACCGGC-3') (SEQ ID NO: 14) and SLF-D (5'-GACAGTATCGTAATTACG-3') (SEQ ID NO: 15); and (ii) a primer comprising the reverse complement of primer HISGCH and SLF-D as above. Alternatively, PCR with SLF-A (5'-CTAACTCTAGCTGCATTG-3') (SEQ ID NO:24) (or SLF-G) and SLF-D (or SLF-F) could be used to produce a diagnostic shift in product length after PCR. The SLF1 deleted version of CTY145 is designated CUY104; the SLF1 deleted version of CUY101 is designated CUY105; the SLF1 deleted version of CUY103 is designated CUY106; and, the SLF1 deleted version of ZMY60 is designated CUY107.

Figure 9:
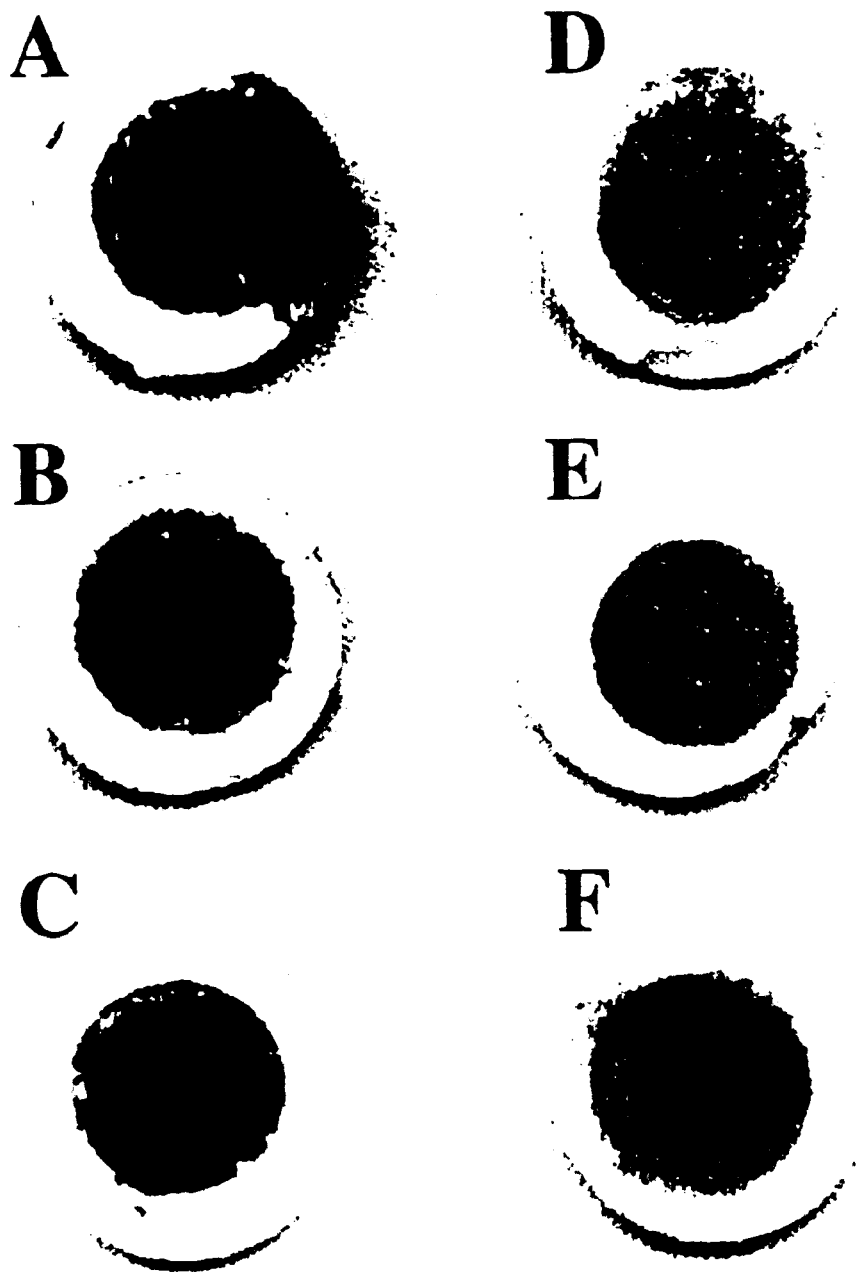
FIG. 9A–F is a photograph of cell filtrates demonstrating the effect of deleting the SLF1 gene on biomineralization by yeast.

Cultures of yeast strains CTY145, CUY101, CUY103, CUY104, CUY105, and CUY106 were cultured in 5 ml of complete synthetic media (CSM) supplemented with 500 mM $CuSO_4$ at 30° C. in a rollerdrum apparatus at a speed of approximately 60 revolutions per minute. At 24 and 48 hours, the cultures were pelleted and resuspended in fresh CSM media containing 500 mM $CuSO_4$. After 96 hours of incubation, cells were collected onto filter paper and the supernatant was removed by suction through the filter paper. Biomineralization is inferred by the presence of a darkened cell pellet, indicating the biomineralization of the soluble copper to copper sulfide (CuS) which has been shown to be deposited on the cell surface. Strains CTY145, CUY 101, and CUY 103 (A, B, and C, respectively in FIG. 9) contain the wild-type SLF1 gene, as demonstrated by their dark color. Strains CUY104, CUY105, and CUY106, in which the SLF1 gene has been deleted, show considerably lighter coloration after collection on filter paper, indicating an ablation of copper biomineralization activity.

Figure 10:
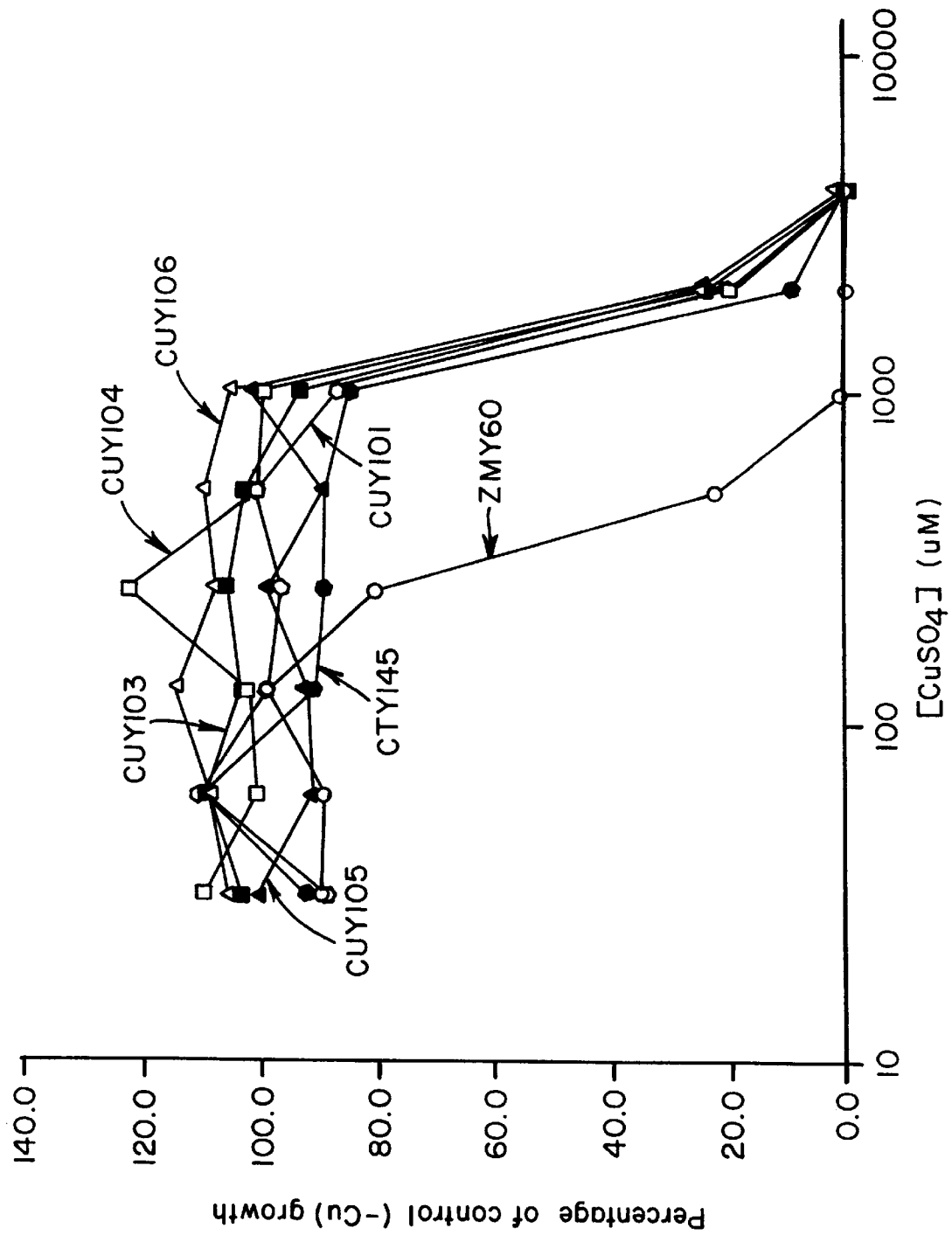
FIG. 10 is a graph demonstrating the effect of copper sulfate on the growth of yeast strains which express and do not express the SLF1 gene.

Single colonies of each yeast strain described above were picked from YPD plates and grown overnight in YPD media at 30° C. with shaking. Cultures were diluted to an absorbance at 600 nm of 0.02 in CSM media containing various concentrations of $CuSO_4$. Cultures were grown for 24 hours at 30° C. in a rollerdrum apparatus at approximately 60 revolutions per minute. The absorbance of each culture at 600 nm, which is a measure of cell density (i.e., the number of cells in a culture) was measured. The results of the cell density assays are shown in FIG. 10, and is expressed as a percentage of the cell density achieved in cells with no added copper sulfate.

EXAMPLE 3

Method for Stable Replacement of the Promoter Element of any Gene of Interest with a Copper-Inducible Promoter The following procedures were performed to stably replace the promoter element of any yeast gene of interest. The strategy is designed to avoid: (1) the use of URA3 as a selectable marker, which precludes its use in future selection procedures; (2) the requirement for a naturally occurring unique restriction site in the coding sequence of the subject gene; (3) the need for multiple subclonings; and (4) the need for constant maintenance of URA3 selection in order to prevent loss of the inserted sequence, which would result in restoration of the original promoter elements.

A single or double-PCR strategy was devised. Instead of a single crossover event, the method requires that a double crossover occur in order to achieve integration into the yeast genome. Although a double crossover event is less likely to occur, once it has occurred the resulting transformed haploid yeast strain does not have to be maintained under selection. HIS3 is used as a marker to avoid using URA3 unnecessarily; in addition, the HIS3 gene is relatively short and therefore comparatively easy to amplify.

A plasmid designated pCU3 was constructed which contains a functional HIS3 gene (including upstream sequences) in inverted orientation to, and upstream from, the ANB1 promoter. The ANB1 promoter was fused upstream (i.e., 5' to) sequences encoding ubiquitin tag elements. For this purpose, the BamHI/PstI fragment of pUC8-Sc2676 was subcloned into pUC 19. Then, the EcorI-KpnI fragment of ZM168, which contains the ANB1 promoter and the ubiquitin tag regions, was subcloned into the plasmid.

Figure 2B:
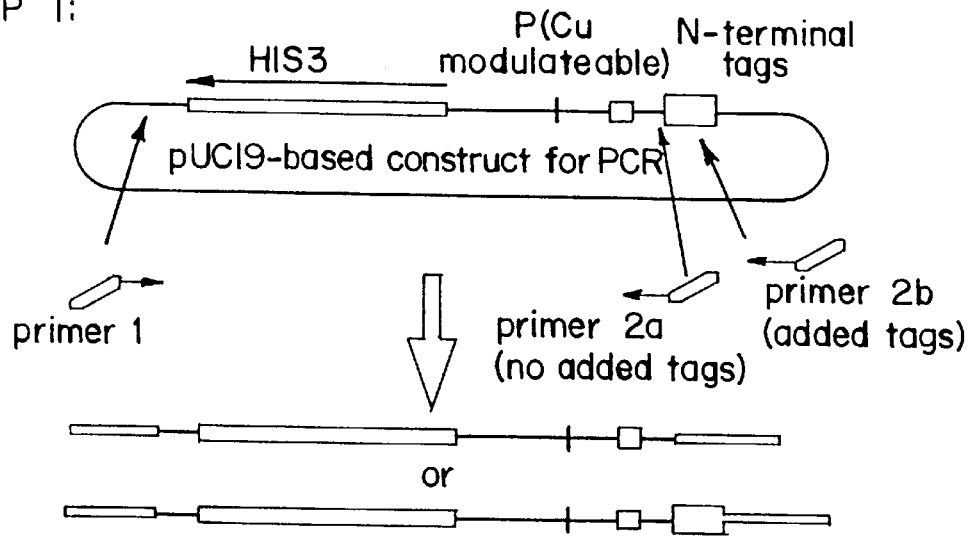
FIG. 2 (parts I–III) is a schematic illustration of the single- or double-round PCR strategy of the present invention that is used to construct a copper-inducible promoter element for any gene of interest. For single round PCR, primer pairs 1 and either 2a or 2b are used to produce the transforming DNA. For the double-round PCR, primer pairs 2a or 2b are used with additional primers corresponding to sequences located 400–1000 bp upstream or downstream of the ATG start site to prepare long primers which are then used in a second round of PCR to produce transforming DNA.
Figure 2C:
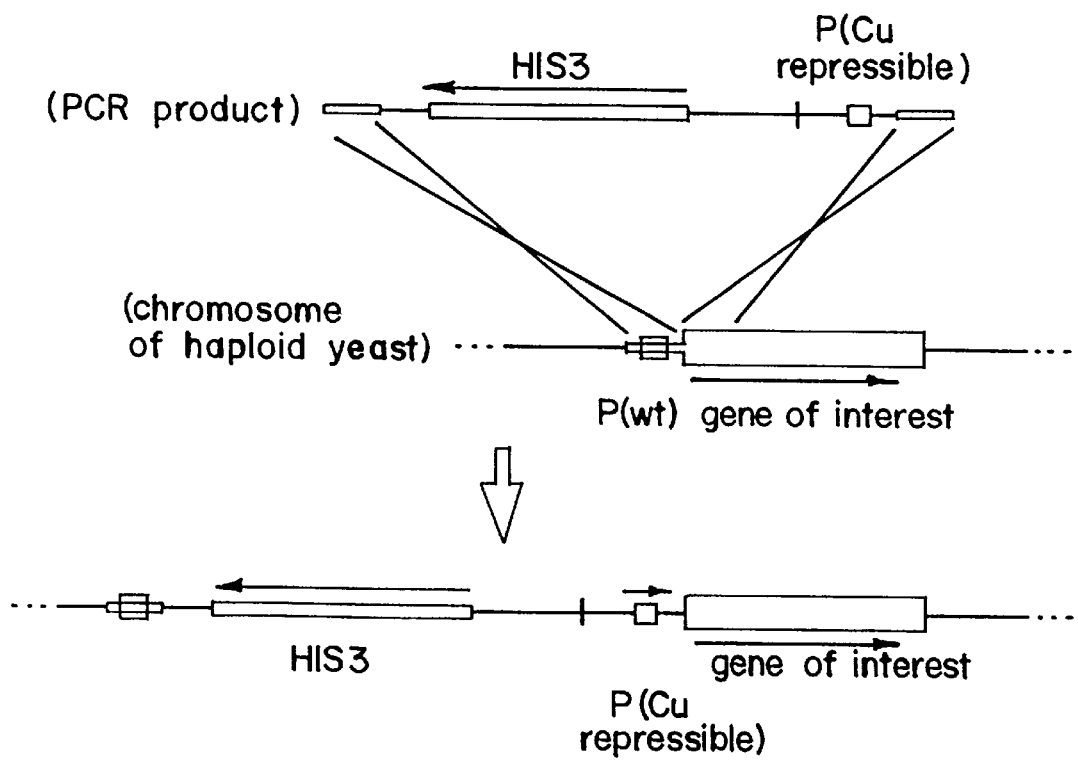

Primers were designed for use in either a one-step or two-step PCR strategy. (FIG. 2).

One-Step PCR Strategy: 100-mer oligonucleotides were synthesized. Primer 1 contains 80 bp of target sequence from the gene of interest, which is obtained from knowledge of the DNA sequence immediately 5' to the protein-coding sequence of the gene, together with 20 bp of plasmid sequence. A second set of primers comprising sequences from the non-coding strand is synthesized. These oligonucleotides, which are designated either Primer 2b (5'-CCAGACTACGCTTCGATATCG-3') (SEQ ID NO: 16) ("+Tag") or Primer 2a (5'-CACACTAAAACATCGATATT-3') (SEQ ID NO: 17) ("NO TAG"), are then fused to 18–20 bp of the protein-coding sequence of a gene of interest, beginning with the initiator ATG codon. In this case, "Tag" refers to the presence or absence of the ubiquitin tag.

Primer pairs 1 and 2a or 1 and 2b are used to amplify a DNA fragment from pCU3, producing a fragment consisting of genomic 5'NTS (non-translated sequence) followed by HIS3 in an inverted orientation, ANB1 promoter, and either a fragment of the ORF or a tag sequence fused in frame to a fragment of the ORF. Transformation of haploid yeast strains with these sequences, followed by double crossover, leads to integration into the genome. This results in insertion of HIS3, the ANB1 promoter and (in some cases) the tag sequence 5' to the gene of interest.

Using this approach, no DNA sequence is lost and no sequence is duplicated, thereby considerably lessening the likelihood that the inserted sequence will be spontaneously deleted. After selection with HIS3, the presence and orientation of the insert is confirmed using PCR. Because the integration requires a double crossover, selection by HIS selection should not be required to maintain the genotype.

Two-Step PCR Strategy: For the two step strategy, Primer 2a or 2b is fused to 18–20 bp of the ORF of a gene of interest, beginning with the initial ATG of the ORF. Either primer, and a second primer comprising 18–20 nucleotides that is the reverse complement of a sequence 400–1000 bp downstream, are used to amplify a 400–1000 bp fragment that is the reverse complement of the ORF and has a 3' tag complementary to the sequence in pCU3 such that the sequence is fused in frame to the tags or is fused in frame in place of the tags.

The fragment corresponding to the opposite end is produced by fusing a primer designated "Universal HIS3-2STEP" (5'-CAGGCATGCAAGCTTGGCGT-3') (SEQ ID NO: 18) to an 18- to 20-mer representing the reverse complement immediately 5' of the starting ATG of the ORF. This fragment is used in conjunction with a primer identical to 18–20 nucleotides comprising a sequence 400–1000 bp 5' to the starting ATG to amplify a fragment whose 3' end is complementary to the 3' end of the HIS3 gene in pCU3.

The two fragments are then used to amplify pCU3, producing a fragment comprising a length of genomic 5'NTS followed by HIS3 in inverted orientation, ANB1 promoter and either a length of the ORF or a tag sequence fused in frame to a length of the ORF.

Transformation with this sequence and double crossover leads to integration into the genome, which results in the insertion or HIS3, the ANB1 promoter and (in some cases) the tag sequence. Using this approach, no DNA sequence is lost and no sequence is duplicated, thereby greatly lessening the likelihood of spontaneous deletion. After selection with HIS3, the presence and orientation of the insert is confirmed with PCR. Because the integration requires a double crossover, HIS selection should not be required to maintain the genotype.

EXAMPLE 4

Figure 8:
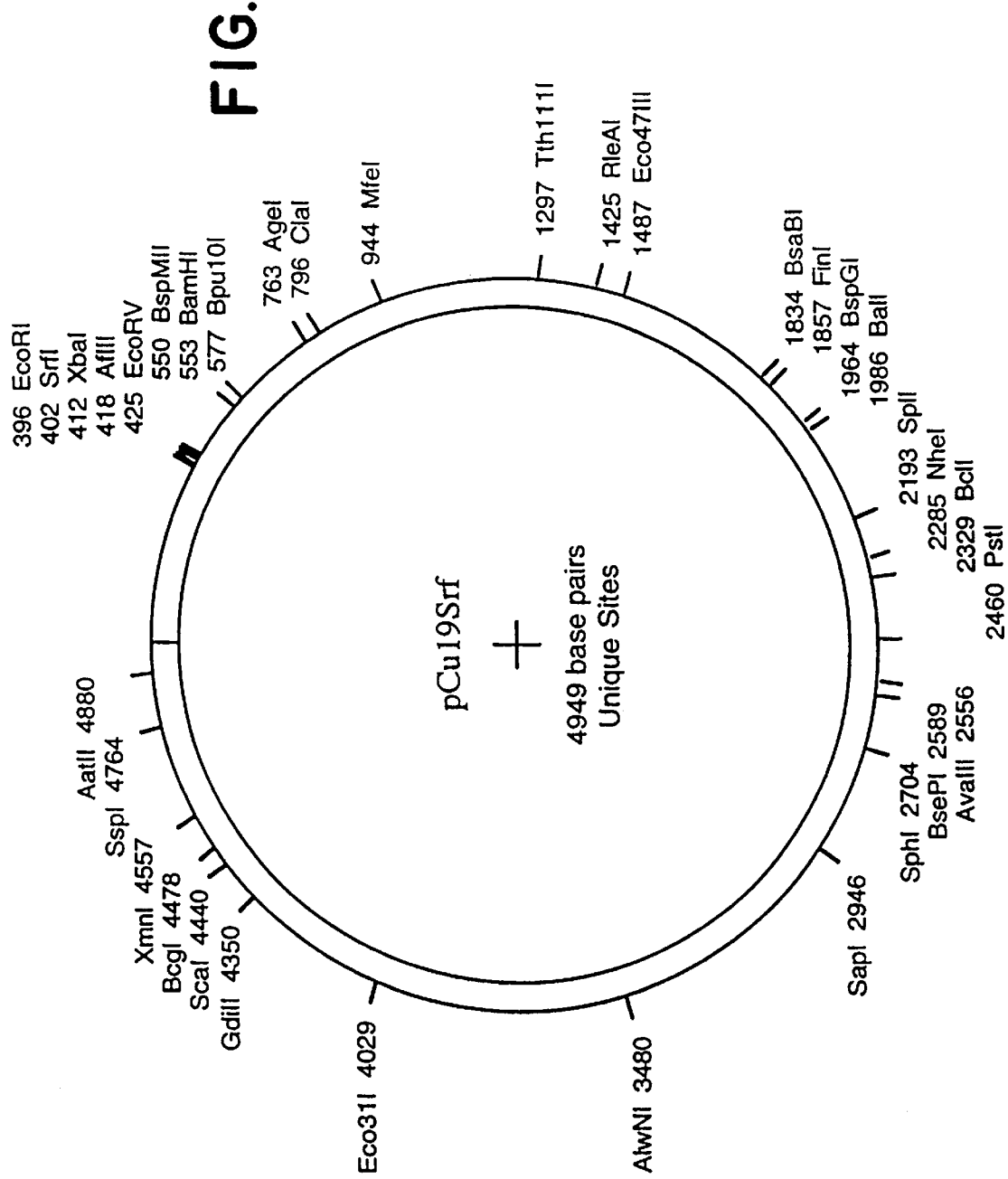
FIG. 8 is a restriction map of the pCU19Srf vector (SEQ ID NO:22), showing the unique restriction enzyme cutting sites.

Alternative Method for Stable Replacement of the Promoter Element of any Gene of Interest with a Copper-Inducible Promoter PCR primers are designed to amplify sequences of the target gene to result in a "shuffled gene" arrangement (FIG. 6) in the vector pCU19Srf (FIG. 8). The PCR primers that can be used will vary from 18 to 36 nucleotides in length, and will preferentially have a GC content of at least 50 percent. When primers, which are 18 to 36 nucleotides in length have a low GC content, the primers can be made 3 to 6 nucleotides longer than those with at least a 50% GC content.

PCR primers are dissolved in sterile water at a concentration of 1 mg/ml. Genomic DNA from *S. cerevisiae* is diluted to various concentrations in sterile water. Taq DNA polymerase (Promega Biotech, Madison, Wis.) is typically used for the primary PCR reaction, but other thermostable polymerases, such as Vent polymerase (New England Biolabs, Beverly, Mass.) or Pfu polymerase (Stratagene, Carlsbad, Calif.) can also be used.

The shuffled gene of interest is generated by performing two primary PCR reactions. In one, a portion of the target gene which starts about 400 base pairs upstream of the ATG start codon and ends just upstream of the ATG start codon is amplified. In the second primary PCR reaction, a portion of the target gene that starts at or that is just upstream of the ATG start codon and that ends about 400 base pairs downstream of the ATG start codon is amplified. A typical primary PCR reaction will include 10 µl of 10X Taq buffer, 10 µl of 25 mM deoxynucleoside triphosphates, 10 µl of 25 mM MgCl$_2$, 1 µl of S. cerevisiae genomic DNA, and 1 µl of primer pairs (Primers 1 and 2, or primers 3 and 4) at 100 µg/ml, and 66 µl of sterile water.

Typically, primer 1 will consist (from the 5' to the 3' end) of a seven nucleotide sequence, then a NotI restriction endonuclease cleavage site (or a restriction site susceptible to cleavage by another rare-cutting enzyme), followed by 10 or 11 nucleotides which are identical to the top strand of the gene of interest about 400 base pairs upstream of the ATG start codon of the target gene. The seven nucleotides at the 5' end of primer 1 are complementary to the 7 nucleotides immediately 3' of the NotI site in primer 4.

Primer 2 will have the sequence of the bottom strand of the gene of interest, just upstream of the ATG start codon, and will comprise about 18 to about 21 nucleotides.

Primer 3 will have the sequence of the top strand of the target gene either at or very close to the ATG start codon.

Primer 4 will consist of a seven nucleotide sequence at the 5' end, followed by a NotI restriction endonuclease cleavage site (or a restriction site susceptible to cleavage by another rare-cutting enzyme), followed by 10 or 11 nucleotides which are identical to the bottom strand of the gene of interest about 400 base pairs downstream of the ATG start codon. The seven nucleotides at the 5' end of primer 4 are complementary to the 7 nucleotides immediately 3' of the NotI site in primer 1.

Typically, the reaction is initiated by heating the reaction mixtures to 94° C. for 3 to 5 minutes, followed by the addition of 5 units of Taq DNA polymerase. The reaction is then thermocycled reaction mixture through 1 minute at 94° C., 1 minute at 50° C., and 2 minutes at 72° C. for 30 cycles, after which the temperature is reduced to 4° C. The PCR products are run on an agarose gel to determine the conditions that produced a fragment of the appropriate size, typically about 400 base pairs. Modifications of various parameters of the method in order to optimize reaction conditions, such as altering annealing temperatures, salt concentrations, and the like are within the skill of the ordinarily skilled worker.

The secondary PCR reaction uses the primary PCR reaction products as DNA templates. The one end of each of the two primary PCR products are homologous, and when melted, will anneal to each other over a stretch of about 21 base pairs. The primers used for the secondary PCR reaction are primers 2 and 3 used in the primary PCR reactions. Use of these primers will anneal to the ends of the annealed template DNA and allow the PCR reaction to produce a shuffled gene reaction product.

A typical secondary PCR reaction will include 10 µl of 10×Pfu buffer, 10 µl of 25 mM deoxynucleoside triphosphates, 1 µl of primer pairs (i.e., primers 2 and 3 from the primary PCR reaction) at a concentration of 100 µg/ml, 77 µl of sterile water, various dilutions of the primary PCR products, and 1 µl of Pfu polymerase, comprising 2.5 activity units. The PCR conditions are identical to those to be used in the primary reactions, except that the initial heating of the tubes to 94° C. for 3 to 5 minutes is omitted.

The secondary PCR product is electrophoresed through an agarose gel, according to methods well-known in the art, and the appropriate band (of about 800 to 900 base pairs) is cut out. The DNA is then extracted from the gel using, e.g., the Gene Clean kit (Bio101, Vista, Calif.). The extracted, purified DNA is then used for ligation into the vector pCu19Srf (FIGS. 8).

To perform the ligation, the PCR-Script kit from Stratagene (La Jolla, Calif.) is used. pCu19Srf is cut with SrfI restriction endonuclease. The ligation mix contains 100 ng of SrfI cut vector DNA, 1 µl of 10×PCR Script buffer, 0.5 µl ATP, 4 to 6 µl of insert DNA, containing from 100 to 500 ng, 1 µl of T4 DNA ligase, and 1 µl of SrfI. All reagents are provided in the PCR Script kit except for the DNA. However, such reagents are well-known and commercially available from other sources. Three µls of the ligation reaction is transformed into competent DH5α cells, which can be obtained from Gibco/BRL (Rockville, Md.), and the cells are plated on LB medium with 100 µg/ml ampicillin. The plates are incubated at 37° C. for 16 to 18 hours. Single colonies are chosen for restriction enzyme digestion and analysis of the resulting fragments to identify a clone which contains the insert in the proper orientation. A colony that is identified as containing a plasmid with the insert in the proper orientation is selected and is amplified by culturing. The insert-containing plasmid is purified from the bacterial host using the DNA isolation procedure of the Qiagen DNA preparation kit (Qiagen, Hilden, Germany) or other well-known methods for plasmid purification. The purified DNA is digested with NotI restriction endonuclease (or another rare-cutting endonuclease whose restriction site has been engineered into the shuffled gene). The endonuclease is inactivated by heating for 20 minutes at 65° C. The purified, cut DNA is then used to transform S. cerevisiae.

Strain CUY106 (Ace-ROX1, AceUBR1, deltaSLF1, his3delta200, leu2-3,112, ura3-52) is transformed by standard methods with the NotI digested plasmid DNA (FIG. 7). Cells are plated on CSM agar lacking histidine and are incubated at 30° C. for 40 to 48 hours. Single colonies are selected and restreaked for single colonies on the same media. A culture from a single colony is grown in YPD and a genomic DNA is isolated for evaluation by PCR reaction to verify the construction of the strain.

PCR primers for genomic verification are designed so that one primer (Primer 5') at one end of the gene is 5 prime to Primer 1 (above) used to generate the shuffled gene on the plasmid and on the same strand as Primer 1. Another primer (Primer 3') is designed which is 3 prime to Primer 4 (above) and on the same strand as Primer 4. PCR conditions are as those described for Primary PCR (above). Another primer, specific for the plasmid sequence, 5'-ACCCTGGCGCCCAATACG-3' (SEQ ID NO:23), is used in conjunction with Primer 3' to amplify DNA from the mutant strains, i.e., those that contain the shuffled genes. The product of this PCR reaction is typically 600 to 700 base pairs in length.

Wild type genomic DNA and Primer 5' and Primer 3' are used to amplify a 1 to 1.5 kb PCR product. This primer pair should not yield a PCR product from the mutant genomic DNA using these PCR conditions because the product would be too big to amplify (>7 kb).

EXAMPLE 5
Assay for Reversion Frequency in Yeast Strains Engineered with Copper Repressible Genes The following assay was performed to assess the frequency with which a culture maintained under non-selective conditions will revert to a phenotype of non-sensitivity to exogenously added metal ions. Cultures of strains produced by two different methods in different strain backgrounds were grown in the absence of selection, then assayed to determine what percentage of the cells in the culture were no longer sensitive to the addition of copper ions.

Two independent isolates of ZMY71 (ZM71 #1 and ZM71 #2) were used in this assay. ZM71 is derived from ZMY60, and its construction is described in Moqtaderi, Z. et al., Nature 383: 188–191 (1996). The SUA7 gene was operably linked to an ANB1 promoter by a single cross-over strategy in a strain in which ROX1 and UBR1 are activated by the addition of copper to the culture medium. The recombinant strains are maintained by selection on media lacking uracil (-URA). It is known that in the absence of selection, spontaneous recombination results in a strain in which the URA3 gene is lost (reverting to a ura3 phenotype) and regulation of the SUA7 gene by the ANB1 promoter is lost, while wild-type regulation of SUA7 is restored.

Two independent yeast strain isolates (19SG1 and 19SG2) were also used. In these yeast strains the SUA7 gene in strain CUY 106 was operably linked to an ANB1 promoter by the double cross-over strategy as detailed in Example 4. The recombination results in a strain that can be selected for on media lacking histidine (-HIS). Because of the method used to engineer this strain results in an insertion which does not contain any tandem repeats of sequence, it should be less likely that in the absence of selection on -HIS media the strain would revert to a his3 phenotype or regain wild-type regulation of the SUA7 gene.

All strains were streaked from glycerol stocks to the appropriate selective media (uracil free media for ZM71 and histidine free media for the 19SG strains) and were grown for 72 hours at 30° C. Single colonies were picked and inoculated into 2 ml of selective media and were cultured overnight in a rollerdrum at 30° C. The yeast cultures were microcentrifuged for approximately 5 seconds and the pellets were resuspended in two ml of YPD media (non-selective). The cultures were than grown 24 hours at 30° C. in a rollerdrum.

Dilutions of each culture were plated to YPD and CSM plus 1 mM cupric sulfate plates. Plates were incubated for 72 hours at 30° C. and the colonies were counted. YPD plate colony numbers reflect the total cells in the culture, while colonies on the CSM plus 1 mM cupric sulfate plates indicate revertants, i.e., cells which have become insensitive to the copper ion stimulus. Revertants are expressed in the table below as a percentage of total cells observed.

| STRAIN | REVERTANTS |
| --- | --- |
| ZM71 #1 | 0.012% |
| ZM71 #2 | 0.22% |
| 19SG1 | 0.00024% |
| 19SG2 | 0.00042% |

Not all reversions are due to genetic changes at the SUA7 locus. It is also possible that the copper stimulation of UBR1 or ROX1 gene expression can be ablated. However, since the control of these genes is identical in all the strains, any ablation of copper stimulation of these genes appear as background which all strains will share. The change in the reversion frequency at 24 hours in the 19SG strains engineered according the methods of Example 4 demonstrates the improvements that can be achieved by altering gene expression in yeast according the methods disclosed herein.

EXAMPLE 6
Construction of Yeast Strains Containing CYC8-LexA Repressor Under Copper Control The following procedures are performed to produce a yeast strain that expresses a heterologous repressor under copper control. Such strains avoid the potential problems of ROX1-based repressor strains, which include the pleiotropic effects and toxicities of ROX1 and metal ions. In a LexA-based repressor system, the addition of metal ions represses only recombinant genes whose promoters have been engineered to contain the bacterial-derived recognition sequence for LexA (LexA operator). A CYC8-LexA fusion has been shown to repress the transcription of a yeast gene when the LexA operator sequence is placed adjacent to the promoter of the yeast gene (Keleher et al., Cell 68: 709, 1992).

This system comprises two components: (i) a yeast strain which, in the presence of copper, expresses a CYC8-LexA fusion protein or a fusion protein between LexA and a fragment of ROX1 that lacks DNA-binding activity and (ii) a DNA fragment which renders any desired target gene repressible by LexA when introduced upstream of the start of the open reading frame. Notably, this can be achieved even if only a limited amount of sequence information is available.

A repressor fusion protein is constructed so that the DNA-binding domain of LexA (amino acids 1–87) is fused to the N-terminus of the entire CYC8 protein (amino acids 1–966) as well as 23 amino acids derived from the 5' untranslated region of CYC8. This hybrid protein is expressed from a conditionally "inert" locus, such as TRP 1. Alternatively, a fusion protein is constructed so that the DNA-binding domain of LexA is fused to a ROX1 protein which has been mutated so that it no longer binds to ROX 1 recognition sequences, such as those present in the yeast ANB1 promoter.

Figure 3:
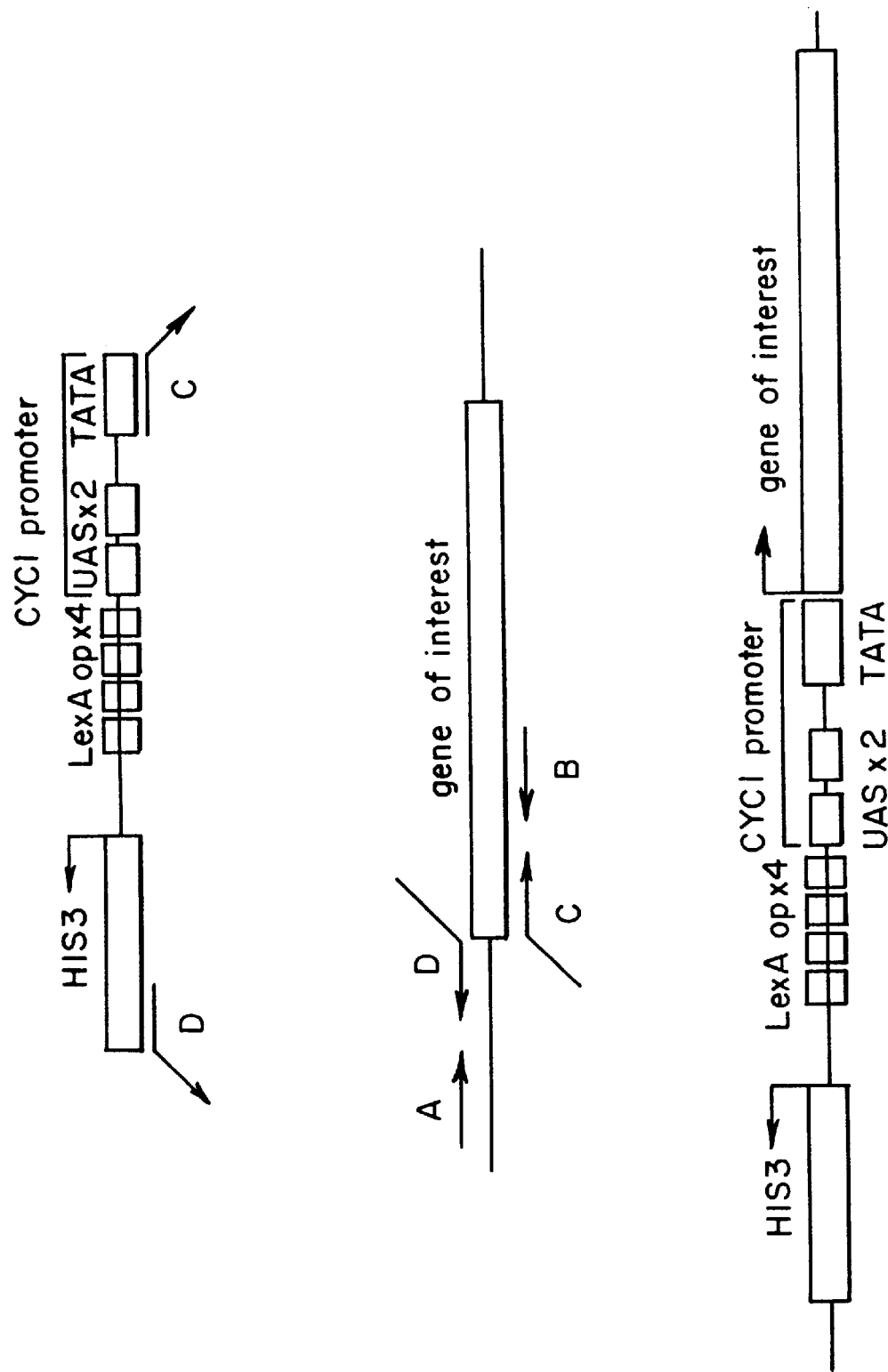
FIG. 3 is a schematic illustration of a PCR primer A–D design strategy that can be used to render a gene encoding a protein of interest repressible by LexA. The upper panel shows the structure of the promoter complex that can be inserted upstream of the gene of interest. The middle panel shows the location of the sequences corresponding to the PCR primers that can be utilized. The lower panel shows the resulting promoter cassette fused to the gene of interest which can be introduced into yeast.

In order to render a particular gene repressible by the hybrid repressor proteins described above, a generic repressible promoter cassette is designed that can be inserted upstream of any gene. The promoter cassette consists of one to several copies of the LexA operator placed upstream of a UAS-containing yeast promoter, such as, e.g., CYCI, adjacent to a gene such as HIS3 which can be used for positive selection. The insertion cassette can be produced by a single- or double-round PCR strategy by analogy to the method shown in FIG. 2. In this case, the point of insertion is upstream of the promoter region and not at the translational start site (FIG. 3).

The repressible promoter is modified so that it will integrate upstream of a given yeast target gene as follows. Four PCR primers are designed based on limited sequence data flanking the 5' end of the gene of interest as shown in FIG. 2.

(i) Primer A is located 100–200 base pairs upstream of the beginning of the open reading frame of the gene, oriented toward the gene.

(ii) Primer B is located 100–200 within the 5' end of the open reading frame, oriented towards the 5' start of the gene.

(iii) Primers C and D contain both sequences specific to each gene as well as sequences homologous to the generic repressible promoter cassette. Primer C contains at its 5'-most end sequences corresponding to the 3' end of the promoter cassette, in this case the 3' end of the CYC1 promoter. The 3' half of primer C contains sequences corresponding to the 5' end of the open reading frame of interest. The 3' end of Primer D consists of the sequence complementary to the sequence just upstream of the gene of interest. The 5' half of Primer D consists of sequences complementary to the left-most end of the promoter cassette, in this case the 3' end of the HIS3 gene.

Typical sequences for primers C and D are:

Primer C: 5'-ACAAATACACACACTAAATTAATAA-TGNNNNNNN-3' (SEQ ID NO:19)

Primer D: 5'-end of HIS3- NNNNNNNNNNNN-3'

Two sets of PCR reactions are performed. In the first set, a fragment of DNA containing the gene of interest and 5' flanking region is used as a template and amplification is performed using Primers A and D or Primers B and C. The resulting fragments are then included in a second round of PCR containing the promoter cassette, both initial PCR products, and Primers A and B. This results in a larger fragment containing the promoter cassette flanked by pieces of DNA that will target the DNA just upstream of the gene of interest (FIG. 3).

Following transformation into yeast and selection for integration, stable integrants produced by sequence-specific recombination into the site of interest can be positively identified by PCR or Southern blot analyses. This strategy produces a conditional locus that is repressible by the LexA fusion proteins described above.

EXAMPLE 7

Demonstration of Cidal and Static Effects of Copper Ion-induced Repression of Gene Expression Three different yeast cell strains were constructed based on the CUY106 strain. The yeast CDC15, SUA7, and ERG11 genes were rendered repressible by copper-ion addition to the growth medium as described above.

Figure 11:
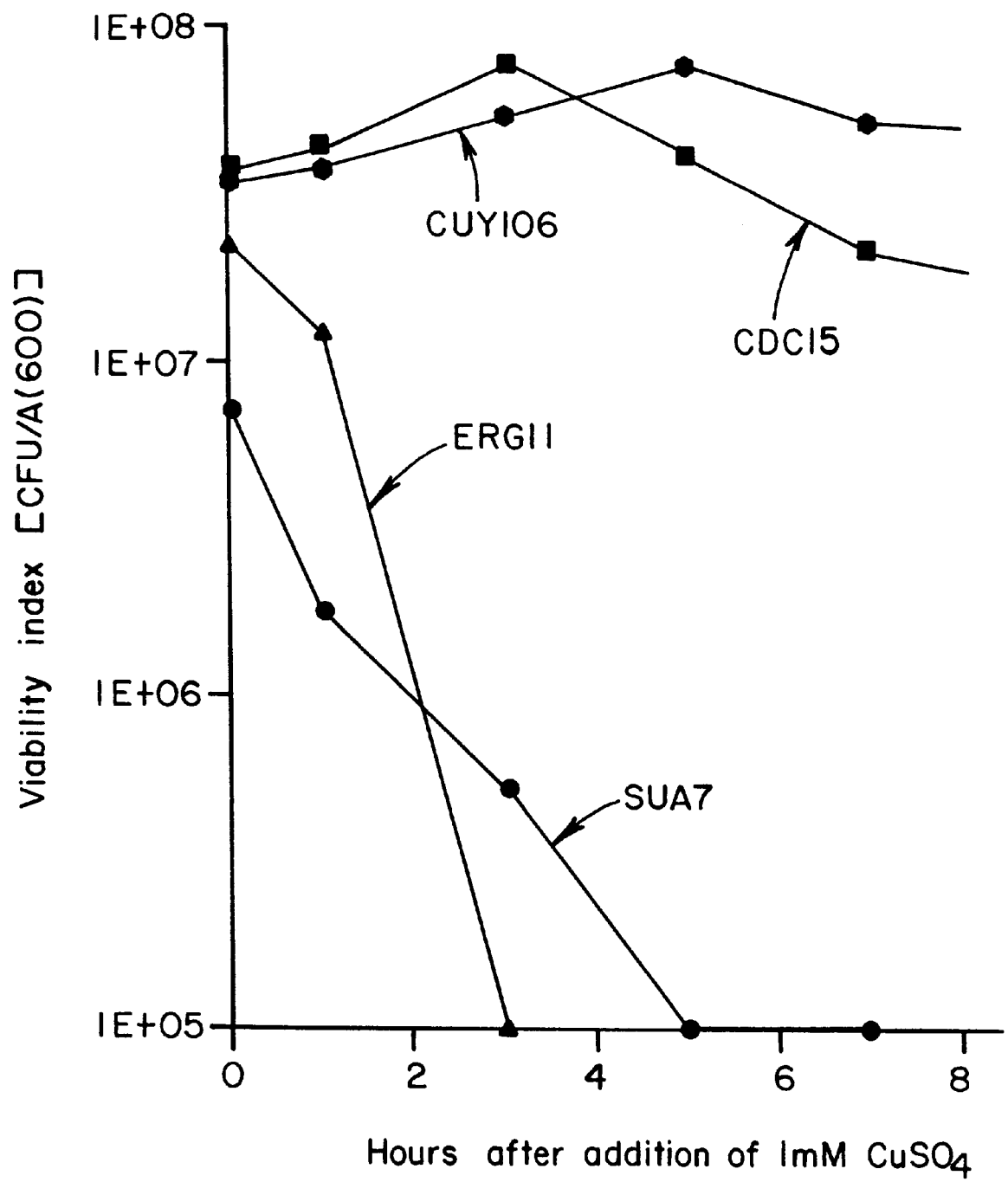
FIG. 11 is a graph showing growth curves for control and recombinant yeast strains which were grown in the presence of copper sulfate.

The viability of each strain was evaluated at several time points over an 8 hour period after the addition of 1 mM copper sulfate to the growth medium by diluting the cells and plating them on YPD medium, without copper sulfate. Yeast colonies were counted after 48 hours of incubation at 30° C. in order to determine the colony forming units (CFU) per ml of original copper sulfate-containing culture medium at the time the yeast cells were harvested and diluted. The CFU/ml value was divided by the measured absorbance of the original copper sulfate-containing growth medium at 600 nm ($A_{600}$) at the time the aliquots were taken for dilution and plating onto YPD medium, yielding a viability index of CFU/$A_{600}$. The limit of detection for CFU/$A_{600}$ is approximately $1 \times 10^5$. FIG. 11 shows the results of the assay, demonstrating that repression of the expression of some genes, such as SUA7 and ERG11, is cidal, i.e., kills, the yeast cells, while repression of expression of other genes, such as the CDC15 gene, only has a static effect on the yeast cells, arresting their growth but not killing them.

We claim:

1. A yeast cell comprising:
   (i) a first gene encoding a transcriptional repressor protein whose expression is under the control of a metal ion-responsive element, wherein expression of said first gene encoding said repressor protein is stimulated by the addition of a metal ion to growth medium of said yeast cell;
   (ii) a second gene encoding a subject protein, wherein expression of said second gene encoding said subject protein is controlled by a transcriptional control sequence whose activity is inhibited by said repressor protein; and
   (iii) a third gene encoding a biomineralization protein, wherein said third gene is inactivated and wherein inactivation of said third gene enhances transcriptional response of said metal ion-responsive element to metal ions in said growth medium of said yeast cell.

2. A yeast cell as defined in claim 1, wherein said transcriptional repressor protein is the protein encoded by the ROX1 gene.

3. A yeast cell as defined in claim 1, wherein said transcriptional control sequence is ANB1 promoter.

4. A yeast cell as defined in claim 1, wherein said biomineralization gene is SLF1.

5. A yeast cell as defined in claim 1, further comprising a fourth gene encoding a protein that targets ubiquitin-containing polypeptides for degradation.

6. A yeast cell as defined in claim 5, wherein said fourth gene is placed under the control of a metal ion-responsive element.

7. A yeast cell as defined in claim 5, wherein said fourth gene is UBR1.

8. A yeast cell as defined in claim 5, wherein said second gene further comprises additional DNA sequences encoding peptides that target proteins for ubiquitin-mediated degradation, wherein said additional DNA sequences are fused in-frame to the gene encoding said subject protein.

9. A yeast cell as defined in claim 1, wherein said transcriptional repressor protein is CYC8-LexA.

10. A yeast cell as defined in claim 1, wherein said gene encoding said transcriptional repressor protein is ROX1-LexA.

11. A yeast cell comprising:
   (i) a first gene encoding a subject protein, the expression of said gene being under the control of a metal ion-responsive element, wherein expression of said first gene is stimulated by the addition of metal ions to growth medium of said yeast cell; and
   (ii) a second gene encoding a biomineralization protein, wherein said second gene is inactivated and wherein inactivation of said second gene enhances the transcriptional response of said metal ion-responsive element to metal ions added to said growth medium of said yeast cell.

12. A yeast cell as defined in claim 11, wherein said biomineralization gene is SLF1.

13. A method for repressing expression of a subject gene in a yeast cell to a predetermined level, said method comprising culturing a yeast cell as defined in claim 1 in the presence of metal ions, wherein said metal ions are present in sufficient concentration to activate said metal ion-responsive element to a level which will result in said predetermined level of repression of expression of said subject gene.

14. A method for repressing expression of a subject gene in a yeast cell to a predetermined level, said method comprising culturing a yeast cell as defined in claim 7 in the presence of metal ions, wherein said metal ions are present in sufficient concentration to activate said metal ion-responsive element to a level which will result in said predetermined level of repression of expression of said subject gene.

15. A method for activating expression of a subject gene in a yeast cell to a predetermined level, said method comprising culturing a yeast cell as defined in claim 11 in the presence of metal ions, wherein said metal ions are present in sufficient concentration to activate said metal ion-responsive element to a level which will result in said predetermined level of activation of expression of said subject gene.

16. The method of claim 13, wherein said metal ions are silver ions.

17. The method of claim 14, wherein said metal ions are silver ions.

18. The method of claim 15, wherein said metal ions are silver ions.

* * * * *

SEQUENCE LISTING

<160> NUMBER OF SEQ ID NOS: 24

<210> SEQ ID NO 1
<211> LENGTH: 19
<212> TYPE: DNA
<213> ORGANISM: Artificial Sequence
<220> FEATURE:
<223> OTHER INFORMATION: LexA operator

<400> SEQUENCE: 1
tactgatgta catacagta                                            19

<210> SEQ ID NO 2
<211> LENGTH: 52
<212> TYPE: DNA
<213> ORGANISM: Artificial Sequence
<220> FEATURE:
<223> OTHER INFORMATION: Artificial LexA operator

<400> SEQUENCE: 2
tcgagtactg tatgtacata cagtaccatg acatacatgt atgtcatgag ct       52

<210> SEQ ID NO 3
<211> LENGTH: 42
<212> TYPE: DNA
<213> ORGANISM: Artificial Sequence
<220> FEATURE:
<223> OTHER INFORMATION: ACE1 binding site

<400> SEQUENCE: 3
taagtctttt ttgctggaac ggttgagcgg aaaagacgca tc                  42

<210> SEQ ID NO 4
<211> LENGTH: 18

```
<212> TYPE: DNA
<213> ORGANISM: Artificial Sequence
<220> FEATURE:
<223> OTHER INFORMATION: ROX-A PCR primer

<400> SEQUENCE: 4
tcacacaaaa gaacgcag                                                   18

<210> SEQ ID NO 5
<211> LENGTH: 18
<212> TYPE: DNA
<213> ORGANISM: Artificial Sequence
<220> FEATURE:
<223> OTHER INFORMATION: ROX-B PCR primer

<400> SEQUENCE: 5
gatgacagct gtggtagg                                                   18

<210> SEQ ID NO 6
<211> LENGTH: 18
<212> TYPE: DNA
<213> ORGANISM: Artificial Sequence
<220> FEATURE:
<223> OTHER INFORMATION: ROX-C PCR primer

<400> SEQUENCE: 6
tcttgccata tggatctg                                                   18

<210> SEQ ID NO 7
<211> LENGTH: 18
<212> TYPE: DNA
<213> ORGANISM: Artificial Sequence
<220> FEATURE:
<223> OTHER INFORMATION: UBR-A PCR primer

<400> SEQUENCE: 7
atcttcggac aaaggcag                                                   18

<210> SEQ ID NO 8
<211> LENGTH: 18
<212> TYPE: DNA
<213> ORGANISM: Artificial Sequence
<220> FEATURE:
<223> OTHER INFORMATION: UBR-B PCR primer

<400> SEQUENCE: 8
gtgtaatttt cgggatcg                                                   18

<210> SEQ ID NO 9
<211> LENGTH: 18
<212> TYPE: DNA
<213> ORGANISM: Artificial Sequence
<220> FEATURE:
<223> OTHER INFORMATION: ROX-C PCR Primer

<400> SEQUENCE: 9
tcttgccata tggatctg                                                   18

<210> SEQ ID NO 10
<211> LENGTH: 33
<212> TYPE: DNA
<213> ORGANISM: Artificial Sequence
<220> FEATURE:
<223> OTHER INFORMATION: SLF-E PCR primer

<400> SEQUENCE: 10
gcgctgcagg tcgacttagc aggcagtttg aac                                  33
```

```
<210> SEQ ID NO 11
<211> LENGTH: 33
<212> TYPE: DNA
<213> ORGANISM: Artificial Sequence
<220> FEATURE:
<223> OTHER INFORMATION: SLF-F PCR primer

<400> SEQUENCE: 11
gcgctgcagg catgcactcc tttccaattg tgc                          33

<210> SEQ ID NO 12
<211> LENGTH: 32
<212> TYPE: DNA
<213> ORGANISM: Artificial Sequence
<220> FEATURE:
<223> OTHER INFORMATION: SLF-G PCR primer

<400> SEQUENCE: 12
gcgagctcgg tacccatac ccctaactct ag                            32

<210> SEQ ID NO 13
<211> LENGTH: 32
<212> TYPE: DNA
<213> ORGANISM: Artificial Sequence
<220> FEATURE:
<223> OTHER INFORMATION: SLF-H PCR primer

<400> SEQUENCE: 13
gcggatcccg gggctctctc gtttatttaa cg                           32

<210> SEQ ID NO 14
<211> LENGTH: 18
<212> TYPE: DNA
<213> ORGANISM: Artificial Sequence
<220> FEATURE:
<223> OTHER INFORMATION: HISGCH PCR primer

<400> SEQUENCE: 14
gatttggtct ctaccggc                                           18

<210> SEQ ID NO 15
<211> LENGTH: 18
<212> TYPE: DNA
<213> ORGANISM: Artificial Sequence
<220> FEATURE:
<223> OTHER INFORMATION: SLF-D PCR primer

<400> SEQUENCE: 15
gacagtatcg taattacg                                           18

<210> SEQ ID NO 16
<211> LENGTH: 21
<212> TYPE: DNA
<213> ORGANISM: Artificial Sequence
<220> FEATURE:
<223> OTHER INFORMATION: PCR primer 2b

<400> SEQUENCE: 16
ccagactacg cttcgatatc g                                       21

<210> SEQ ID NO 17
<211> LENGTH: 20
<212> TYPE: DNA
<213> ORGANISM: Artificial Sequence
<220> FEATURE:
<223> OTHER INFORMATION: PCR primer 2a
```

<400> SEQUENCE: 17
cacactaaaa catcgatatt                                                        20

<210> SEQ ID NO 18
<211> LENGTH: 20
<212> TYPE: DNA
<213> ORGANISM: Artificial Sequence
<220> FEATURE:
<223> OTHER INFORMATION: Universal HIS3-2STEP PCR primer

<400> SEQUENCE: 18
caggcatgca agcttggcgt                                                        20

<210> SEQ ID NO 19
<211> LENGTH: 34
<212> TYPE: DNA
<213> ORGANISM: Artificial Sequence
<220> FEATURE:
<223> OTHER INFORMATION: Primer C typical sequence; n in 28 to 34
      represents any nucleotide

<400> SEQUENCE: 19
acaaatacac acactaaatt aataatgnnn nnnn                                        34

<210> SEQ ID NO 20
<211> LENGTH: 7102
<212> TYPE: DNA
<213> ORGANISM: Artificial Sequence
<220> FEATURE:
<223> OTHER INFORMATION: Plasmid pZM195

<400> SEQUENCE: 20
gaattaattc gagctcggta ccggtgatct tcgctcggcc acaaatcccc tggatatcat           60
tggcctgtcg aggtatcggc cgcgtggaac taccgggaat tactatgcaa acaattgga          120 aatctggtag gaaaaccttg ttctagaact tggcgattgc tgacaaagaa gaaaagggcc          180
tattgttgct gcctcttttg ttgttcttcc tcgtattgtc ttgccggtgt tctttgtgtc          240
ttttgtgtgt aggttcttac tattatagtg ctctttgcta ttatattttc ttcgttttca          300
ctttgcgtaa tgtaacggtc ttaaacaaag tttttttttt ttcgctcttg catttttctt          360
ttctgctcta tcttatttgc taattgtagt ttcagaagtt ttaccttaaa tatagcacta          420
ttttccagtt ttaatgtttc ttctcattgc tttcttttat aattttcgca tataattata          480
catttacggt gtcttaactc tccctcttca cccctcatta ttccagaaaa tactaatact          540
tcttcacaca aaagaacgca gttagacaat caacaatgac tagtagtttt tcttgaacca          600
aagaaaggtc accagaggca atagactctt caatctcatt gattctttgc ttggcttctg          660
cagtggacga gaactggcc tttttgccta acttctcctc aatttggttg tttttttctct         720 tgatttgagc atccaattgc ttaatagagt cgtgaatgtt gcttctacgg gttttcaagt          780
cagcttggat cttgatgatc tccttgttct tatcctgtaa cttcttacgt tcttgttggg          840
tggtatcgtt gacctggtgt tgatcgattt gctttctaat taaaccgatt tcagtgtcga          900 ttttttttcaa ttgaacgtta agagtgtcca atttcttgtc tctaacggag acatctgggc        960
gcttgaactt gtgttgttgg gaggacatgg caatggctgt gttgttagaa aatatgctat         1020
tacgttgata aaaggaggaa aggtgaaatc agttcaaaaa tgtgaatgaa actgaacgaa         1080
gaaatgacca gaatgagtga aaaatggaga tggagggca aaatgaaaaa aaaaaaagg          1140 atgaacctaa aatagaaaat agactccgtc gtactttaat gctatgtata acgcaaccaa         1200

```
gcaattttcg aaactcaatt tggcttataa atgttcgaga taaaatgcga attacgtgtt      1260
caacgtcgtc gagatcagtt atttttttc acgccacagt gcgggtaagc aattttttcgc     1320 gtaccaccac cattacacat gtataatgta tataggctta ttatgtatgt ttgtgctact     1380
ttatatgacg gttatttaca agttagaata ttatctatta acaatgcagt agccacgctt     1440
acgtttagtg agtcaacaat gggttctggg gcccgattgc ctttctcaat gccaccaaag     1500
ggaatttcga cgaagaagtc actcctcatc ttcaaattcg ttcttacgcc ctggctttcg     1560
ttccccacca ctagaacaac aggcagctcg ttacataatc cgttcaaatc gtgcatgcta     1620 atagttttc caacagtgta tttttctgac gtggcattag ctaagtggct tgtaataaac     1680
gtccagccac ccatttcttg tgatttagta aaaaactcta acggtttatc aacgtaaaat     1740
atgggcagaa gttcgagggc cccactgctt gtcttggaca ccacaggcgt caaaggagag     1800
cagtttcttc tcgacatcac aatgaagtca acccccagga agtaagcgct tctaataatg     1860
gcaccgatat tgtgagggtc agttatttca tccagatata acccgagagg aaacttctta     1920
gcgtctgttt tcgtaccata aggcagttca tgaggtatat tttcgttatt gaagcccagc     1980
tcgtgaatgc ttaatgctgc tgaactggtg tccatgtcgc ctaggtacgc aatctccaca     2040
ggctgcaaag gttttgtctc aagagcaatg ttattgtgca ccccgtaatt ggtcaacaag     2100
tttaatctgt gcttgtccac cagctctgtc gtaaccttca gttcatcgac tatctgaaga     2160
aatttactag gaatagtgcc atggtacagc aaccgagaat ggcaatttct actcgggttc     2220
agcaacgctg cataaacgct gttggtgccg tagacatatt cgaagatagg attatcattc     2280
ataagtttca gagcaatgtc cttattctgg aacttggatt tatggctctt ttggtttaat     2340
ttcgcctgat tcttgatctc ctttagcttc tcgacgtggg cctttttctt gccatatgga     2400
tctgaattct agtctttttt gctggaacgg ttgagcggaa aagacgcatc gaattcgagc     2460
tcgttagcga ttggcattat cacataatga attatacatt atataaagta atgtgatttc     2520
ttcgaagaat atactaaaaa atgagcaggc aagataaacg aaggcaaagg acggtatcga     2580
tatcaatgaa tcctaaatcc tctacaccta agattccaag acccaagaac gcatttattc     2640
tgttcagaca gcactaccac aggatcttaa tagacgaatg gaccgctcaa ggtgtggaaa     2700 tacccccataa ttcaaacatt tctaaaatta ttggtacgaa gtggaagggc ttacaaccgg     2760
aagataaggc acactgggaa aatctagcgg agaaggagaa actagaacat gaaaggaagt     2820
atcctgaata caaatacaag ccggtaagaa agtctaagaa gaagcaacta cttttgaagg     2880
aaatcgagca acagcagcag caacaacaga agaacagca gcagcagaaa cagtcacaac     2940
cgcaattaca acagcccttt aacaacaata tagttcttat gaaaagagca cattctcttt     3000
caccatcttc ctcggtgtca agctcgaaca gctatcagtt ccaattgaac aatgatctta     3060
agaggttgcc tattccttct gttaatactt ctaactatat ggtctccaga tcctctagag     3120
tcgacctgca ggcatgcaag cttggcgtaa tcatggtcat agctgtttcc tgtgtgaaat     3180
tgttatccgc tcacaattcc acacaacata cgagccggaa gcataaagtg taaagcctgg     3240
ggtgcctaat gagtgagcta actcacatta attgcgttgc gctcactgcc cgctttccag     3300
tcgggaaacc tgtcgtgcca ggggggatcc actagttcta gagtcgaccg gcatgcaagc     3360
ttggcgtaat catggtcata gctgtttcct gtgtgaaatt gttatccgct cacaattcca     3420
cacaacatac gagccggaag cataaagtgt aaagcctggg gtgcctaatg agtgagctaa     3480
ctcacattaa ttgcgttgcg ctcactgccc gctttccagt cgggaaacct gtcgtgccag     3540
ctgcattaat gaatcggcca acgcgcgggg agaggcggtt tgcgtattgg gcgctcttcc     3600
```

```
gcttcctcgc tcactgactc gctgcgctcg gtcgttcggc tgcggcgagc ggtatcagct      3660
cactcaaagg cggtaatacg gttatccaca gaatcagggg ataacgcagg aaagaacatg      3720
tgagcaaaag gccagcaaaa ggccaggaac cgtaaaaagg ccgcgttgct ggcgtttttc      3780
cataggctcc gcccccctga cgagcatcac aaaaatcgac gctcaagtca gaggtggcga      3840
aacccgacag gactataaag ataccaggcg tttccccctg gaagctccct cgtgcgctct      3900
cctgttccga ccctgccgct taccggatac ctgtccgcct ttctcccttc gggaagcgtg      3960
gcgctttctc atagctcacg ctgtaggtat ctcagttcgg tgtaggtcgt tcgctccaag      4020
ctgggctgtg tgcacgaacc ccccgttcag cccgaccgct gcgccttatc cggtaactat      4080
cgtcttgagt ccaacccggt aagacacgac ttatcgccac tggcagcagc cactggtaac      4140
aggattagca gagcgaggta tgtaggcggt gctacagagt tcttgaagtg gtggcctaac      4200
tacggctaca ctagaaggac agtatttggt atctgcgctc tgctgaagcc agttaccttc      4260
ggaaaaagag ttggtagctc ttgatccggc aaacaaacca ccgctggtag cggtggtttt      4320
tttgtttgca agcagcagat tacgcgcaga aaaaaggat ctcaagaaga tcctttgatc      4380
ttttctacgg ggtctgacgc tcagtggaac gaaaactcac gttaagggat tttggtcatg      4440
agattatcaa aaaggatctt cacctagatc cttttaaatt aaaaatgaag ttttaaatca      4500
atctaaagta tatatgagta aacttggtct gacagttacc aatgcttaat cagtgaggca      4560
cctatctcag cgatctgtct atttcgttca tccatagttg cctgactccc cgtcgtgtag      4620
ataactacga tacgggaggg cttaccatct ggccccagtg ctgcaatgat accgcgagac      4680
ccacgctcac cggctccaga tttatcagca ataaaccagc cagccggaag ggccgagcgc      4740
agaagtggtc ctgcaacttt atccgcctcc atccagtcta ttaattgttg ccgggaagct      4800
agagtaagta gttcgccagt taatagtttg cgcaacgttg ttgccattgc tacaggcatc      4860
gtggtgtcac gctcgtcgtt tggtatggct tcattcagct ccggttccca acgatcaagg      4920
cgagttacat gatcccccat gttgtgcaaa aaagcggtta gctccttcgg tcctccgatc      4980
gttgtcagaa gtaagttggc cgcagtgtta tcactcatgg ttatggcagc actgcataat      5040
tctcttactg tcatgccatc cgtaagatgc ttttctgtga ctggtgagta ctcaaccaag      5100
tcattctgag aatagtgtat gcggcgaccg agttgctctt gcccggcgtc aatacgggat      5160
aataccgcgc cacatagcag aactttaaaa gtgctcatca ttggaaaacg ttcttcgggg      5220
cgaaaactct caaggatctt accgctgttg agatccagtt cgatgtaacc cactcgtgca      5280
cccaactgat cttcagcatc ttttactttc accagcgttt ctgggtgagc aaaaacagga      5340
aggcaaaatg ccgcaaaaaa gggaataagg gcgacacgga aatgttgaat actcatactc      5400
ttcctttttc aatattattg aagcatttat cagggttatt gtctcatgag cggatacata      5460
tttgaatgta tttagaaaaa taaacaaata ggggttccgc gcacatttcc ccgaaaagtg      5520
ccacctgacg tctaagaaac cattattatc atgacattaa cctataaaaa taggcgtatc      5580
acgaggccag ttttcaatt caattcatca tttttttttt attctttttt ttgatttcgg      5640
tttctttgaa attttttga ttcggtaatc tccgaacaga aggaagaacg aaggaaggag      5700
cacagactta gattggtata tatacgcata tgtagtgttg aagaaacatg aaattgccca      5760
gtattcttaa cccaactgca cagaacaaaa acatgcagga aacgaagata atcatgtcg      5820 aaagctacat ataaggaacg tgctgctact catcctagtc ctgttgctgc caagctattt      5880
aatatcatgc acgaaaagca acaaacttg tgtgcttcat tggatgttcg taccaccaag      5940
gaattactgg agttagttga agcattaggt cccaaaattt gtttactaaa aacacatgtg      6000
```

-continued

```
gatatcttga ctgattttc catggagggc acagttaagc cgctaaaggc attatccgcc      6060
aagtacaatt ttttactctt cgaagacaga aaatttgctg acattggtaa tacagtcaaa      6120
ttgcagtact ctgcgggtgt atacagaata gcagaatggg cagacattac gaatgcacac      6180
ggtgtggtgg gcccaggtat tgttagcggt ttgaagcagg cggcagaaga agtaacaaag      6240
gaacctagag gccttttgat gttagcagaa ttgtcatgca agggctccct atctactgga      6300
gaatatacta agggtactgt tgacattgcg aagagcgaca aagattttgt tatcggcttt      6360
attgctcaaa gagacatggg tggaagagat gaaggttacg attggttgat tatgacaccc      6420
ggtgtgggtt tagatgacaa gggagacgca ttgggtcaac agtatagaac cgtggatgat      6480
gtggtctcta caggatctga cattattatt gttggaagag gactatttgc aaagggaagg      6540
gatgctaagg tagagggtga acgttacaga aaagcaggct gggaagcata tttgagaaga      6600
tgcggccagc aaaactaaaa aactgtatta taagtaaatg catgtatact aaactcacaa      6660
attagagctt caatttaatt atatcagtta ttacccgccc tttcgtctcg cgcgtttcgg      6720
tgatgacggt gaaaacctct gacacatgca gctcccggag acggtcacag cttgtctgta      6780
agcggatgcc gggagcagac aagcccgtca gggcgcgtca gcgggtgttg gcgggtgtcg      6840
gggctggctt aactatgcgg catcagagca gattgtactg agagtgcacc atatgcggtg      6900
tgaaataccg cacagatgcg taaggagaaa ataccgcatc aggcgccatt cgccattcag      6960
gctgcgcaac tgttgggaag ggcgatcggt gcgggcctct tcgctattac gccagctggc      7020
gaaaggggga tgtgctgcaa ggcgattaag ttgggtaacg ccagggtttt cccagtcacg      7080
acgttgtaaa acgacggcca gt                                               7102
```

<210> SEQ ID NO 21
<211> LENGTH: 7333
<212> TYPE: DNA
<213> ORGANISM: Artificial Sequence
<220> FEATURE:
<223> OTHER INFORMATION: Plasmid pZM197

<400> SEQUENCE: 21

```
gaattaattc gagctcggta ccagttgcca caccacaaaa gtcgaaaaag gctaagaaac       60
caaagaataa ggtactaagt acccaggcgc tactaagacc aacgagattg ccacgaaact      120
agaggaaacc aaattgtaag catagcttaa tccgttttca cgattcataa tataataaat      180
aagaaaagat atatcatata aacgttataa aattaataac cgggtaagtg tagaaaagtg      240
atgcgacggt ttattttctc ttcctcttgc gattgaattt aacttgcaga tagtgaccat      300
aaggcaacta cccagtggca aacagttttg ataacgccca gtacatcaac gagcgagtat      360
aaagactttg gtacatttta aaaggaaac atatattgtt ttcattgcta gaccctttta      420
gtctcacctc aataaaactg ctttattcct cattgggctt tttattcttt aattttgcat      480
acttatagcg tgaaactggg catttaacaa agcaaaacta ttttaatagt agcatcctgc      540
tttctttgcc cctccttctt attgcgatac attattaagt tttttttacca cctttcttcc      600 ttttcttcg catcttcgga caaaggcagt tgaagttac tgtatcctat tagttgacta      660
ttttctctca ctgaagtccc taatctttac aggtcacaca aattacatag acattccaa      720 ctagtagttt ttcttgaacc aaagaaaggt caccagaggc aatagactct tcaatctcat      780
tgattctttg cttggcttct gcagtggacg agaacttggc cttttttgcct aacttctcct      840 caatttggtt gttttttctc ttgatttgag catccaattg cttaatagag tcgtgaatgt      900
tgcttctacg ggttttcaag tcagcttgga tcttgatgat ctccttgttc ttatcctgta      960
```

```
acttcttacg ttcttgttgg gtggtatcgt tgacctggtg ttgatcgatt tgctttctaa      1020
ttaaaccgat ttcagtgtcg atttttttca attgaacgtt aagagtgtcc aatttcttgt      1080
ctctaacgga gacatctggg cgcttgaact tgtgttgttg ggaggacatg gcaatggctg      1140
tgttgttaga aaatatgcta ttacgttgat aaaaggagga aaggtgaaat cagttcaaaa      1200
atgtgaatga aactgaacga agaaatgacc agaatgagtg aaaaatggag atggaggggc      1260
aaaatgaaaa aaaaaaaaag gatgaaccta aaatagaaaa tagactccgt cgtactttaa      1320
tgctatgtat aacgcaacca agcaattttc gaaactcaat ttggcttata atgttcgag       1380 ataaaatgcg aattacgtgt tcaacgtcgt cgagatcagt tatttttttt cacgccacag      1440
tgcgggtaag caattttcg cgtaccacca ccattacaca tgtataatgt atataggctt       1500
attatgtatg tttgtgctac tttatatgac ggttatttac aagttagaat attatctatt      1560
aacaatgcag tagccacgct tacgtttagt gagtcaacaa tgggttctgg ggcccgattg      1620
cctttctcaa tgccaccaaa gggaattcg acgaagaagt cactcctcat cttcaaattc       1680
gttcttacgc cctggctttc gttccccacc actagaacaa caggcagctc gttacataat      1740
ccgttcaaat cgtgcatgct aatagttttt ccaacagtgt attttctga cgtggcatta       1800 gctaagtggc ttgtaataaa cgtccagcca cccatttctt gtgatttagt aaaaaactct      1860 aacgtttat caacgtaaaa tatgggcaga agttcgaggg ccccactgct tgtcttggac       1920
accacaggcg tcaaaggaga gcagtttctt ctcgacatca caatgaagtc aaccccagg      1980 aagtaagcgc ttctaataat ggcaccgata ttgtgagggt cagttatttc atccagatat     2040
aacccgagag gaaacttctt agcgtctgtt ttcgtaccat aaggcagttc atgaggtata     2100
ttttcgttat tgaagcccag ctcgtgaatg cttaatgctg ctgaactggt gtccatgtcg     2160
cctaggtacg caatctccac aggctgcaaa ggttttgtct caagagcaat gttattgtgc     2220
accccgtaat tggtcaacaa gtttaatctg tgcttgtcca ccagctctgt cgtaaccttc     2280
agttcatcga ctatctgaag aaatttacta ggaatagtgc catggtacag caaccgagaa     2340
tggcaatttc tactcgggtt cagcaacgct gcataaacgc tgttggtgcc gtagacatat     2400
tcgaagatag gattatcatt cataagtttc agagcaatgt ccttattctg gaacttggat     2460
ttatggctct tttggtttaa tttcgcctga ttcttgatct cctttagctt ctcgacgtgg     2520
gcctttttct tgccatatgg atctgaattc tagtcttttt tgctggaacg gttgagcgga     2580
aaagacgcat cgaattcgag ctcgttagcg attggcatta tcacataatg aattatacat     2640
tatataaagt aatgtgattt cttcgaagaa tatactaaaa aatgagcagg caagataaac     2700
gaaggcaaag gacggtatcg ataagcttgg gaattcaaaa tgcccaagaa gaagcggaag     2760
gtccatatgt acccatacga cgttccagac tacgcttctt tgggtggttc tagcccaagc     2820
ttgatatcga attcctgcag cccgggggat cctaacatgt ccgttgctga tgatgattta     2880
ggatctttac aaggtcacat taggagaaca ctgaggtcta ttcataacct ccctatttt      2940 aggtatacga gaggtcctac tgaaagggct gacatgagca gagcccttaa agagttcatt     3000
tacagatatc tatactttgt catttctaac agcggagaga acttacctac tttattcaat     3060
gctcatccaa aacaaaaatt atctaaccca gagcttactg ttttttcctga cagtttagaa    3120 gatgctgtgg atattgataa gataacatct caacaaacta ttccgttta aagatagat       3180 gaatccagaa taggagacgt ccataaacat accggaagaa attgtgggag gaaattcaaa     3240
ataggggaac ccttgtatag gtgtcatgag gtgttgcg atgatacttg tgtgcttgt         3300 attcattgtt ttaatccaaa agatcatgtg aatcatcatg tttgtaccga tatatgtact     3360
```

-continued

```
gaattcgata tcaagcttgg cgtaatcatg gtcatagctg tttcctgtgt gaaattgtta    3420
tccgctcaca attccacaca acatacgagc cggaagcata agtgtaaag cctggggtgc     3480 ctaatgagtg agctaactca cattaattgc gttgcgctca ctgcccgctt tccagtcggg    3540
aaacctgtcg tgccaggggg gatccactag ttctagagtc gaccggcatg caagcttggc    3600
gtaatcatgg tcatagctgt ttcctgtgtg aaattgttat ccgctcacaa ttccacacaa    3660
catacgagcc ggaagcataa agtgtaaagc ctggggtgcc taatgagtga gctaactcac    3720
attaattgcg ttgcgctcac tgcccgcttt ccagtcggga aacctgtcgt gccagctgca    3780
ttaatgaatc ggccaacgcg cggggagagg cggtttgcgt attgggcgct cttccgcttc    3840
ctcgctcact gactcgctgc gctcggtcgt tcggctgcgg cgagcggtat cagctcactc    3900
aaaggcggta atacggttat ccacagaatc aggggataac gcaggaaaga acatgtgagc    3960
aaaaggccag caaaaggcca ggaaccgtaa aaaggccgcg ttgctggcgt ttttccatag    4020
gctccgcccc cctgacgagc atcacaaaaa tcgacgctca gtcagaggt ggcgaaaccc     4080 gacaggacta taaagatacc aggcgtttcc ccctggaagc tccctcgtgc gctctcctgt    4140
tccgaccctg ccgcttaccg gatacctgtc cgcctttctc ccttcgggaa gcgtggcgct    4200
ttctcatagc tcacgctgta ggtatctcag ttcggtgtag gtcgttcgct ccaagctggg    4260
ctgtgtgcac gaaccccccg ttcagcccga ccgctgcgcc ttatccggta actatcgtct    4320
tgagtccaac ccggtaagac acgacttatc gccactggca gcagccactg gtaacaggat    4380
tagcagagcg aggtatgtag gcggtgctac agagttcttg aagtggtggc ctaactacgg    4440
ctacactaga aggacagtat ttggtatctg cgctctgctg aagccagtta ccttcggaaa    4500
aagagttggt agctcttgat ccggcaaaca aaccaccgct ggtagcggtg gtttttttgt    4560
ttgcaagcag cagattacgc gcagaaaaaa aggatctcaa gaagatcctt tgatcttttc    4620
tacgggtctg acgctcagtg gaacgaaaaa ctcacgttaa gggattttgg tcatgagatt    4680
atcaaaaagg atcttcacct agatcctttt aaattaaaaa tgaagtttta aatcaatcta    4740
aagtatatat gagtaaactt ggtctgacag ttaccaatgc ttaatcagtg aggcacctat    4800
ctcagcgatc tgtctatttc gttcatccat agttgcctga ctccccgtcg tgtagataac    4860
tacgatacgg gagggcttac catctggccc cagtgctgca atgataccgc gagacccacg    4920
ctcaccggct ccagatttat cagcaataaa ccagccagcc ggaagggccg agcgcagaag    4980
tggtcctgca actttatccg cctccatcca gtctattaat tgttgccggg aagctagagt    5040
aagtagttcg ccagttaata gtttgcgcaa cgttgttgcc attgctacag gcatcgtggt    5100
gtcacgctcg tcgtttggta tggcttcatt cagctccggt tcccaacgat caaggcgagt    5160
tacatgatcc cccatgttgt gcaaaaaagc ggttagctcc ttcggtcctc cgatcgttgt    5220
cagaagtaag ttggccgcag tgttatcact catggttatg gcagcactgc ataattctct    5280
tactgtcatg ccatccgtaa gatgcttttc tgtgactggt gagtactcaa ccaagtcatt    5340
ctgagaatag tgtatgcggc gaccgagttg ctcttgcccg gcgtcaatac gggataatac    5400
cgcgccacat agcagaactt taaaagtgct catcattgga aaacgttctt cggggcgaaa    5460
actctcaagg atcttaccgc tgttgagatc cagttcgatg taacccactc gtgcacccaa    5520
ctgatcttca gcatctttta ctttcaccag cgtttctggg tgagcaaaaa caggaaggca    5580
aaatgccgca aaaagggaa taagggcgac acggaaatgt tgaatactca tactcttcct    5640
ttttcaatat tattgaagca tttatcaggg ttattgtctc atgagcggat acatatttga    5700
atgtatttag aaaaataaac aaataggggt tccgcgcaca tttccccgaa aagtgccacc    5760
```

-continued

```
tgctaagaaa ccattattat catgacatta acctataaaa ataggcgtat cacgaggcca    5820
gcttttcaat tcaattcatc atttttttt tattctttt tttgatttcg gtttctttga    5880
aatttttttg attcggtaat ctccgaacag aaggaagaac gaaggaagga gcacagactt    5940
agattggtat atatacgcat atgtagtgtt gaagaaacat gaaattgccc agtattctta    6000
acccaactgc acagaacaaa aacatgcagg aaacgaagat aaatcatgtc gaaagctaca    6060
tataaggaac gtgctgctac tcatcctagt cctgttgctg ccaagctatt taatatcatg    6120
cacgaaaagc aaacaaactt gtgtgcttca ttggatgttc gtaccaccaa ggaattactg    6180
gagttagttg aagcattagg tcccaaaatt tgtttactaa aaacacatgt ggatatcttg    6240
actgattttt ccatggaggg cacagttaag ccgctaaagg cattatccgc caagtacaat    6300
tttttactct tcgaagacag aaaatttgct gacattggta atacagtcaa attgcagtac    6360
tctgcgggtg tatacagaat agcagaatgg gcagacatta cgaatgcaca cggtgtggtg    6420
ggcccaggta ttgttagcgg tttgaagcag gcggcagaag aagtaacaaa ggaacctaga    6480
ggccttttga tgttagcaga attgtcatgc aagggctccc tatctactgg agaatatact    6540
aagggtactt tgacattgc gaagagcgac aaagattttg ttatcggctt tattgctcaa    6600
agagacatgg gtggaagaga tgaaggttac gattggttga ttatgacacc cggtgtgggt    6660
ttagatgaca agggagacgc attgggtcaa cagtatagaa ccgtggatga tgtggtctct    6720
acaggatctg acattattat tgttggaaga ggactatttg caagggaag ggatgctaag    6780 gtagagggtg aacgttacag aaaagcaggc tgggaagcat atttgagaag atgcggccag    6840
caaaactaaa aaactgtatt ataagtaaat gcatgtatac taaactcaca aattagagct    6900
tcaatttaat tatatcagtt attacccgcc ctttcgtctc gcgcgtttcg gtgatgacgg    6960
tgaaaacctc tgacacatgc agctcccgga gacggtcaca gcttgtctgt aagcggatgc    7020
cgggagcaga caagcccgtc agggcgcgtc agcgggtgtt ggcgggtgtc ggggctggct    7080
taactatgcg gcatcagagc agattgtact gagagtgcac catatgcggt gtgaaatacc    7140
gcacagatgc gtaaggagaa ataccgcat caggcgccat cgccattca ggctgcgcaa    7200 ctgttgggaa gggcgatcgg tgcgggcctc ttcgctatta cgccagctgg cgaaaggggg    7260
atgtgctgca aggcgattaa gttgggtaac gccagggttt cccagtcac gacgttgtaa    7320 aacgacggcc agt                                                       7333
```

<210> SEQ ID NO 22
<211> LENGTH: 4949
<212> TYPE: DNA
<213> ORGANISM: Artificial Sequence
<220> FEATURE:
<223> OTHER INFORMATION: Plasmid pCU19Srf

<400> SEQUENCE: 22

```
tcgcgcgttt cggtgatgac ggtgaaaacc tctgacacat gcagctcccg gagacggtca     60
cagcttgtct gtaagcggat gccgggagca gacaagcccg tcaggcgcgc tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgcccgggcg atctagactt    420
aagcgatatc gaagcgtagt ctggaacgtc gtatgggtag gaatcggcca acgcgcgggg    480
```

-continued

```
agaggcggtt tgcgtattgg gcgccagggt ggttttttctt ttcaccagtg agacgggcaa    540
cagccaagct ccggatccgt gcctaccacc tcttagcctt agcacaagat gtaaggtgga    600
ctccttctga atgttgtaat cagacagcgt tctaccgtct tctagctgct taccggcaaa    660
gatcaatctt tgttgatctg gagggatacc ttccttgtct tgaattttcg acttaacgtt    720
gtcgatggta tcggaagatt caacttccaa tgttatggtt ttaccggtca aagtcttgac    780
gaaaatctgc ataatatcga tgttttagtg tgtgaatgaa ataggtgtat gttttctttt    840
tgctagacaa taattaggaa caaggtaagg gaactaaagt gtagaataag attaaaaaag    900
aagaacaagt tgaaaaggca agttgaaatt tcaagaaaaa agtcaattga agtacagtaa    960
attgacctga atatatctga gttccgacaa caatgagttt accgaagaga acaatggaat   1020
aggaaacttt gaacgaagaa aggaaagcag gaaaggaaaa aatttttagg ctcgagaaca   1080 ataggcaaa aaaacaggca acgaacgaac aatggaaaaa cgaaaaaaaa aaaacacaga   1140
aaagaatgca gaaagttgta aactgaaaaa aaaaaaaaaa aggtgaacac aggaaaaaaa   1200
ataaaaaaaa aaaaaaagga ggacgaaaca aaaaagtgaa aaaaaatgaa aattttttttg   1260 gaaaaccaag aaatgaatta tatttccgtg tgagacgaca tcgtcgaata tgattcaggt   1320
acccgggctg ttccctagca tgtacgtgag cgtatttcct tttaaaccac gacgctttgt   1380
cttcattcaa cgtttcccat tgtttttttc tactattgct ttgctgtggg aaaaacttat   1440
cgaaagatga cgactttttc ttaattctcg ttttaagagc ttggtgagcg ctaggagtca   1500
ctgccaggta tcgtttgaac acggcattag tcagggaagt cataacacag tccttcccg    1560 caattttctt tttctattac tcttggcctc ctctagtaca ctctatattt ttttatgcct   1620
cggtaatgat tttcattttt tttttccac ctagcggatg actctttttt tttcttagcg    1680
attggcatta tcacataatg aattatacat tatataagt aatgtgattt cttcgaagaa    1740
tatactaaaa aatgagcagg caagataaac gaaggcaaag atgacagagc agaaagccct   1800
agtaaagcgt attacaaatg aaaccaagat tcagattgcg atctctttaa agggtggtcc   1860
cctagcgata gagcactcga tcttcccaga aaaagaggca gaagcagtag cagaacaggc   1920
cacacaatcg caagtgatta acgtccacac aggtatagg tttctggacc atatgataca    1980
tgctctggcc aagcattccg gctggtcgct aatcgttgag tgcattggtg acttacacat   2040
agacgaccat cacaccactg aagactgcgg gattgctctc ggtcaagctt ttaaagaggc   2100
cctactggcg cgtggagtaa aaaggtttgg atcaggattt gcgcctttgg atgaggcact   2160
ttccagagcg gtggtagatc tttcgaacag gccgtacgca gttgtcgaac ttggtttgca   2220
aagggagaaa gtaggagatc tctcttgcga gatgatcccg catttcttg aaagcttgc    2280 agaggctagc agaattaccc tccacgttga ttgtctgcga ggcaagaatg atcatcaccg   2340
tagtgagagt gcgttcaagg ctcttgcggt tgccataaga gaagccacct cgcccaatgg   2400
taccaacgat gttccctcca ccaaaggtgt tcttatgtag tgacaccgat tatttaaagc   2460
tgcagcatac gatatatata catgtgtata tatgtatacc tatgaatgtc agtaagtatg   2520
tatacgaaca gtatgatact gaagatgaca aggtaatgca tcattctata cgtgtcattc   2580
tgaacgaggc gcgctttcct ttttcttt tgcttttct ttttttttct cttgaactcg      2640 agaaaaaaa tataaaagag atggaggaac gggaaaaagt tagttgtggt gataggtggc   2700
aaggcatgca agcttggcgt aatcatggtc atagctgttt cctgtgtgaa attgttatcc   2760
gctcacaatt ccacacaaca tacgagccgg aagcataaag tgtaaagcct ggggtgccta   2820
atgagtgagc taactcacat taattgcgtt gcgctcactg cccgctttcc agtcgggaaa   2880
```

| | |
|---|---|
| cctgtcgtgc cagctgcatt aatgaatcgg ccaacgcgcg gggagaggcg gtttgcgtat | 2940 |
| tgggcgctct tccgcttcct cgctcactga ctcgctgcgc tcggtcgttc ggctgcggcg | 3000 |
| agcggtatca gctcactcaa aggcggtaat acggttatcc acagaatcag gggataacgc | 3060 |
| aggaaagaac atgtgagcaa aaggccagca aaaggccagg aaccgtaaaa aggccgcgtt | 3120 |
| gctggcgttt ttccataggc tccgcccccc tgacgagcat cacaaaaatc gacgctcaag | 3180 |
| tcagaggtgg cgaaacccga caggactata agataccag gcgtttcccc ctggaagctc | 3240 |
| cctcgtgcgc tctcctgttc cgaccctgcc gcttaccgga tacctgtccg cctttctccc | 3300 |
| ttcgggaagc gtggcgcttt ctcaatgctc acgctgtagg tatctcagtt cggtgtaggt | 3360 |
| cgttcgctcc aagctgggct gtgtgcacga accccccgtt cagcccgacc gctgcgcctt | 3420 |
| atccggtaac tatcgtcttg agtccaaccc ggtaagacac gacttatcgc cactggcagc | 3480 |
| agccactggt aacaggatta gcagagcgag gtatgtaggc ggtgctacag agttcttgaa | 3540 |
| gtggtggcct aactacggct acactagaag gacagtattt ggtatctgcg ctctgctgaa | 3600 |
| gccagttacc ttcggaaaaa gagttggtag ctcttgatcc ggcaaacaaa ccaccgctgg | 3660 |
| tagcggtggt ttttttgttt gcaagcagca gattacgcgc agaaaaaaag gatctcaaga | 3720 |
| agatcctttg atcttttcta cggggtctga cgctcagtgg aacgaaaact cacgttaagg | 3780 |
| gattttggtc atgagattat caaaaaggat cttcacctag atccttttaa attaaaaatg | 3840 |
| aagttttaaa tcaatctaaa gtatatatga gtaaacttgg tctgacagtt accaatgctt | 3900 |
| aatcagtgag gcacctatct cagcgatctg tctatttcgt tcatccatag ttgcctgact | 3960 |
| ccccgtcgtg tagataacta cgatacggga gggcttacca tctggcccca gtgctgcaat | 4020 |
| gataccgcga gacccacgct caccggctcc agatttatca gcaataaacc agccagccgg | 4080 |
| aagggccgag cgcagaagtg gtcctgcaac tttatccgcc tccatccagt ctattaattg | 4140 |
| ttgccgggaa gctagagtaa gtagttcgcc agttaatagt ttgcgcaacg ttgttgccat | 4200 |
| tgctacaggc atcgtggtgt cacgctcgtc gtttggtatg gcttcattca gctccggttc | 4260 |
| ccaacgatca aggcgagtta catgatcccc catgttgtgc aaaaaagcgg ttagctcctt | 4320 |
| cggtcctccg atcgttgtca gaagtaagtt ggccgcagtg ttatcactca tggttatggc | 4380 |
| agcactgcat aattctctta ctgtcatgcc atccgtaaga tgcttttctg tgactggtga | 4440 |
| gtactcaacc aagtcattct gagaatagtg tatgcggcga ccgagttgct cttgcccggc | 4500 |
| gtcaatacgg gataataccg cgccacatag cagaacttta aaagtgctca tcattggaaa | 4560 |
| acgttcttcg gggcgaaaac tctcaaggat cttaccgctg ttgagatcca gttcgatgta | 4620 |
| acccactcgt gcacccaact gatcttcagc atcttttact ttcaccagcg tttctgggtg | 4680 |
| agcaaaaaca ggaaggcaaa atgccgcaaa aaagggaata agggcgacac ggaaatgttg | 4740 |
| aatactcata ctcttccttt ttcaatatta ttgaagcatt tatcagggtt attgtctcat | 4800 |
| gagcggatac atatttgaat gtatttagaa aaataaacaa ataggggttc cgcgcacatt | 4860 |
| tccccgaaaa gtgccacctg acgtctaaga accattatt atcatgacat aacctataa | 4920 |
| aaataggcgt atcacgaggc cctttcgtc | 4949 |

<210> SEQ ID NO 23
<211> LENGTH: 18
<212> TYPE: DNA
<213> ORGANISM: Artificial Sequence
<220> FEATURE:
<223> OTHER INFORMATION: PCR Primer

<400> SEQUENCE: 23

```
accctggcgc ccaatacg                                            18

<210> SEQ ID NO 24
<211> LENGTH: 18
<212> TYPE: DNA
<213> ORGANISM: PcArtificial Sequence
<220> FEATURE:
<223> OTHER INFORMATION: PCR Primer

<400> SEQUENCE: 24
ctaactctag ctgcattg                                            18
```